US008962320B2

(12) United States Patent  
Terzic et al.

(10) Patent No.: US 8,962,320 B2  
(45) Date of Patent: Feb. 24, 2015

(54) TREATING CARDIOVASCULAR TISSUE

(75) Inventors: Andre Terzic, Rochester, MN (US); Atta Behfar, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/433,095

(22) Filed: Mar. 28, 2012

(65) Prior Publication Data

US 2012/0178164 A1 Jul. 12, 2012

Related U.S. Application Data

(62) Division of application No. 11/572,874, filed as application No. PCT/US2005/026800 on Jul. 29, 2005, now Pat. No. 8,173,118.

(60) Provisional application No. 60/680,775, filed on May 12, 2005, provisional application No. 60/592,871, filed on Jul. 30, 2004.

(51) Int. Cl.
| | |
|---|---|
| *C12N 5/0735* | (2010.01) |
| *C12N 5/077* | (2010.01) |
| *A61K 38/30* | (2006.01) |
| *A61K 38/18* | (2006.01) |
| *A61K 38/20* | (2006.01) |
| *A61K 38/48* | (2006.01) |

(52) U.S. Cl.
CPC ............ *A61K 38/30* (2013.01); *A61K 38/1825* (2013.01); *A61K 38/1841* (2013.01); *A61K 38/1875* (2013.01); *A61K 38/204* (2013.01); *A61K 38/2093* (2013.01); *A61K 38/4833* (2013.01); *A61K 35/545* (2013.01)
USPC .......................................... 435/377; 435/325

(58) Field of Classification Search
CPC combination set(s) only.
See application file for complete search history.

(56) References Cited

U.S. PATENT DOCUMENTS

| | | | |
|---|---|---|---|
| 5,839,438 | A | 11/1998 | Graettinger et al. |
| 6,833,269 | B2 | 12/2004 | Carpenter |
| 7,425,448 | B2 * | 9/2008 | Xu ................................. 435/377 |
| 7,452,718 | B2 * | 11/2008 | Gold et al. ..................... 435/377 |
| 7,732,199 | B2 * | 6/2010 | Xu et al. ........................ 435/366 |
| 7,763,464 | B2 * | 7/2010 | Xu ................................. 435/377 |
| 8,071,380 | B2 | 12/2011 | Cossu et al. |
| 8,158,421 | B2 * | 4/2012 | Passier et al. ................. 435/377 |
| 2002/0039557 | A1 | 4/2002 | White |
| 2002/0061837 | A1 | 5/2002 | Lough et al. |
| 2003/0224345 | A1 | 12/2003 | West et al. |
| 2003/0229908 | A1 | 12/2003 | Cibelli et al. |
| 2005/0164382 | A1 | 7/2005 | Xu |
| 2007/0274970 | A1 | 11/2007 | Gordon et al. |
| 2008/0019944 | A1 | 1/2008 | Terzic et al. |
| 2008/0057028 | A1 | 3/2008 | Alitalo et al. |
| 2010/0009399 | A1 | 1/2010 | Sartipy et al. |
| 2010/0166714 | A1 | 7/2010 | Chien et al. |
| 2010/0189697 | A1 | 7/2010 | Terzic et al. |
| 2011/0117065 | A1 | 5/2011 | Terzic et al. |
| 2012/0100533 | A1 | 4/2012 | Terzic et al. |
| 2012/0178164 | A1 | 7/2012 | Terzic et al. |

FOREIGN PATENT DOCUMENTS

| | | |
|---|---|---|
| JP | 2002-511094 | 4/2002 |
| JP | 2007-517831 | 7/2007 |
| JP | 2007-537692 | 12/2007 |
| WO | WO 2006/015127 | 2/2005 |
| WO | WO 2005/038454 | 4/2005 |
| WO | WO 2005/090558 | 9/2005 |
| WO | WO 2006/032054 | 3/2006 |
| WO | WO 2006/081190 | 8/2006 |
| WO | WO 2007/012009 | 1/2007 |
| WO | WO 2008/109839 | 9/2008 |
| WO | WO 2009/145761 | 12/2009 |
| WO | WO 2009/151907 | 12/2009 |
| WO | WO 2010/133686 | 11/2010 |
| WO | WO 2010/135555 | 11/2010 |

OTHER PUBLICATIONS

Abbott et al., "Stromal Cell—Derived Factor-1 Plays a Critical Role in Stem Cell Recruitment to the Heart After Myocardial Infarction but Is Not Sufficient to Induce Homing in the Absence of Injury," *Circulation*, 2004, 110:3300-3305.
Abdel-Latif et al., "Adult bone marrow-derived cells for cardiac repair: a systematic review and meta-analysis," *Arch intern Med.*, 2007, 167:989-997.
Assmus et al., "Transcoronary transplantation of progenitor cells after myocardial infarction," *N. Engl. J. Med.*, 2006, 355:1222-1232.
Ayach et al. "CXCR4 improves cardiac remodeling and neovascularization and regulated inflammatory and progenitor stem cell mobilization post-myocardial infarction," *J. Cardial Failure*, 2006, 12(6):S43 (Abstract only).
Baba et al. "Flk1 + cardiac stem/progenitor cells derived from embryonic stem cells improve cardiac function in a dilated cardiomyopathy mouse model," *Cardiovasc. Res.*, 2007, 76(1):119-131.
Baldwin et al., "Myogenic cytodifferentiation of the precardiac mesoderm in the rat," *Differentiation*, 1991, 47:163-172.
Barabasi and Oltvai, "Network biology: understanding the cell's functional organization," *Nat. Rev. Genet.*, 2004, 5:101-113.
Bartunek et al. "Pretreatment of adult bone marrow mesenchymal stem cells with cardiomyogenic growth factors and repair of the chronically infracted myocardium," *Am. J. Phys: Heart and Circ. Phys.*, 2007 292 (2):H1095-H1104.
Behfar et al. "Guided Cardiopoiesis Enhances Therapeutic Benefit of Bone Marrow Human Mesenchymal Stem Cells in Chronic Myocardial Infraction," *J. Amer. College of Cardiology*, 2010, 56(9): 721-734.

(Continued)

*Primary Examiner* — Daniel C Gamett
(74) *Attorney, Agent, or Firm* — Fish & Richardson P.C.

(57) ABSTRACT

This document provides methods and materials for treating cardiovascular tissue. For example, stem cells, compositions containing stem cells, methods for obtaining stem cells, compositions for generating stem cells expressing particular markers, and methods for repairing cardiovascular tissue are provided.

9 Claims, 14 Drawing Sheets

(56) References Cited

OTHER PUBLICATIONS

Behfar et al., "Guided stem cell cardiopoietic: Discovery and translation," *J Mol and Cell Cardioogy*, 2008, 45:523-529.

Behfar et al., "Administration of Allogenic Stem Cells Dosed to Secure Cardiogenesis and Sustained Infarct Repair," *Ann. N.Y. Acad. Sci.*, 2005, 1049:189-198.

Beqqali et al., "Genome-wide transcriptional profiling of human embryonic stem cells differentiating to cardiomyocytes," *Stem Cells*, 2006, 24:1956-1967.

Brewer et al., "GATA factors lie upstream of Nkx 2.5 in the transcriptional regulatory cascade that effects cardiogenesis," *Stem Cells Dev.*, 2005, 14:425-439.

Buckingham et al., "Building the mammalian heart from two sources of myocardial cells," *Nat. Rev. Genet.*, 2005, 6:826-835.

Ceradini and Gurtner, "Homing to hypoxia: HIF-1 as a mediator of progenitor cell recruitment to injured tissue," *Trends Cardiovasc. Med.*, 2005, 15:57-63.

Ceradini et al., "Progenitor cell trafficking is regulated by hypoxic gradients through HIF-1induction of SDF-1," *Nat. Med.*, 2004, 10:858-864.

Chen et al., "Myocardin: a component of a molecular switch for smooth muscle differentiation," *J. Mol. Cell Cardiol.*, 2002, 34:1345-1356.

Chung et al., "Mitochondrial oxidative metabolism is required for the cardiac differentiation of stem cells," *Nat. Clin. Pract. Cardiovasc. Med.*, Feb. 2007, 4Suppl(1):S60-67.

Compernolle et al., "Cardia bifida, defective heart development and abnormal neural crest migration in embryos lacking hypoxia-inducible factor-1α," *Cardiovasc. Res.*, 2003, 60:569-579.

Diaz and Gulino, "WHIM syndrome: a defect in CXCR4 signaling," *Curr. Allergy Asthma Rep.*, 2005, 5:350-355.

Eisenberg and Eisenberg, "An in vitro analysis of myocardial potential indicates that phenotypic plasticity is an innate property of early embryonic tissue," *Stem Cells Dev.*, 2004, 13:614-624.

Ema et al., "Deletion of the selection cassette, but not cis-acting elements, in targeted F1k1-lacZ allele reveals F1k1 expression in multipotent mesodermal progenitors," *Blood*, 2006, 107:111-117.

Faustino et al., "Genomic chart guiding embryonic stem cell cardiopoiesis," *Genome Biol.*, 2008, 9(1):R6.

Felgner et al., "Enhanced gene delivery and mechanism studies with a novel series of cationic lipid formulations," *J. Biol. Chem.*, 1994, 269:2550-2561.

Gorlin et al., "WHIM syndrome, an autosomal dominant disorder: clinical, hematological, and molecular studies," *Am. J. Med. Genet.*, 2000, 91:368-376.

Hartmann et al., "The role of adhesion molecules and chemokine receptor CXCR4 (CD 184) in small cell lung cancer," *J. Biol. Regul. Homeost. Agents.*, 2004, 18:126-130.

Hernandez et al., "Mutations in the chemokine receptor gene CXCR4 are associated with WHIM syndrome, a combined immunodeficiency disease," *Nat. Genet.*, 2003, 34:70-74.

Huber et al., "Haemangioblast commitment is initiated in the primitive streak of the mouse embryo," *Nature*, 2004, 432:625-630.

Janssens et al., "Autologous bone marrow-derived stem-cell transfer in patients with ST-segment elevation myocardial infarction: double-blind, randomised controlled trial," *Lancet*, 2006, 367:113-121.

Jiang et al., "Pluripotency of mesenchymal stem cells derived from adult marrow," *Nature*, 2002, 418:41-49.

Kaltman et al., "Multipotent flk-1(+) cardiovascular progenitor cells give rise to the cardiomyocyte, endothelial, and vascular smooth muscle lineages," *Dev. Cell*, 2006, 11:723-732.

Kawai et al., "Efficient cardiomyogenic differentiation of embryonic stem cell by fibroblast growth factor 2 and bone morphogenetic protein 2," *Circ. J.*, 2004, 68:691702.

Kay et al., "Gene therapy," *Proc. Natl. Acad. Sci. USA*, 1997, 94:12744-12746.

Kirby, "Molecular embryogenesis of the heart," *Pediatr. Dev. Pathol.*, 2002, 5:516-543.

Kofidis et al., "Insulin-like growth factor promotes engraftment, differentiation, and functional improvement after transfer of embryonic stem cells for myocardial restoration," *Stem Cells*, 2004, 22:1239-1245.

Kolossov et al., "Engraftment of engineered ES cell-derived cardiomyocytes but not BM cells restores contractile function to the infarcted myocardium," *J. Exp. Med.*, 2006, 203:2315-2327.

Kucia et al., "Bone marrow as a source of circulating CXCR4+ tissue-committed stem cells," *Biol. Cell*, 2005, 97:133-146.

Kucia et al., "Trafficking of normal stem cells and metastasis of cancer stem cells involve similar mechanisms: pivotal role of the SDF-I-CXCR4 axis," *Stem Cells*, 2005, 23:879-894.

Kulbe et al., "The chemokine network in cancer—much more than directing cell movement," *Int. J. Dev. Biol.*, 2004, 48:489-496.

Laflamme and Murry, "Regenerating the heart," *Nat. Biotechnol.*, 2005, 23:845-856.

Lapidot and Kollet, "The essential roles of the chemokine SDF-1 and its receptor CXCR4 in human stem cell homing and repopulation of transplanted immune-deficient NOD/SCID and NOD/SCID/B2m(null) mice," *Leukemia*, 2002, 16:1992-2003.

Lapidot et al., "How do stem cells find their way home?" *Blood*, 2005, 106:1901-1910.

Lapidot, "Mechanism of human stem cell migration and repopulation of NOD/SCID and B2mnull NOD/SCID mice. The role of SDF-1/CXCR4 interactions," *Ann. N.Y. Acad. Sci.*, 2001, 938:83-95.

Lev et al. "Differentiation Pathways in Human Embryonic Stem Cell-Derived Cardiomyocytes," *Ann. N.Y. Acad. Sci.*, 2005 1047:50-65.

Lough and Sugi, "Endoderm and heart development," *Dev. Dyn.*, 2000, 217:327-342.

Lough et al., "Combined BMP-2 and FGF-4, but neither factor alone, induces cardiogenesis in non-precardiac embryonic mesoderm," *Dev. Biol.*, 1996, 178:198-202.

Lunde et al., "Intracoronary injection of mononuclear bone marrow cells in acute myocardial infarction," *N. Engl. J. Med.*, 2006, 355:1199-1209.

Ma et al. "Intramyocardial delivery of human CD133+ cells in a SCID mouse cryoninjury model: Bone marrow vs. cord blood-derived cells," *Cardiovascular Research*, 2006, 71:158-169.

McGrath et al., "Embryonic expression and function of the chemokine SDF-1 and its receptor, CXCR4," *Dev. Biol.*, 1999, 213:442-456.

Menard et al., "Transplantation of cardiac-committed mouse embryonic stem cells to infarcted sheep myocardium: a preclinical study," *Lancet*, 2005, 366:1005-1012.

Meyer et al., "Intracoronary bone marrow cell transfer after myocardial infarction: eighteen months' follow-up data from the randomized, controlled BOOST (BOne marrOw transfer to enhance ST-elevation infarct regeneration) trial," *Circulation*, 2006, 113:1287-1294.

Molkentin et al., "Direct activation of a GATA6 cardiac enhancer by Nkx2.5: evidence for a reinforcing regulatory network of Nkx2.5 and GATA transcription factors in the developing heart," *Dev. Biol.*, 2000, 217:301-309.

Moretti et al., "Multipotent embryonic isll+ progenitor cells lead to cardiac, smooth muscle, and endothelial cell diversification," *Cell*, 2006, 127:1151-1165.

Mummery et al. "Cardiomyocyte differentiation of mouse and human embryonic stem cells," *J. Anatomy*, 2002, 200(part 3):233-242.

Nagasawa et al., "Defects of B-celllymphopoiesis and bone-marrow myelopoiesis in mice lacking the CXC chemokine PBSF/SDF-1," *Nature*, 1996, 382:635-638.

Nakajima et al. "Transplantation of Flkl-postitive embryonic stem cells improves cardiac function after acute myocardial infarction in mice," *J. Heart and Lung Transplant.*, 2005, 24(2):594 (Abstract only).

Nelson et al., "Improved cardiac function in infarcted mice after treatment with pluripotent embryonic stem cells," *Anat. Rec.*, 2006, 288:1216-1224.

Nelson et al. "CXCR4 (+)/FLK-1 (+) biomarkers select a cardiopoietic lineage from embryonic stem cells," *Stem Cells*, 2008, 26(6):1464-1473.

(56) References Cited

OTHER PUBLICATIONS

Perez-Terzic et al., "Stem cells transform into a cardiac phenotype with remodeling of the nuclear transport machinery," Nat. Clin. Pract. Cardiovasc. Med., 2007, 4(Suppl 1):S68-S76.
Pillarisetti and Gupta, "Cloning and relative expression analysis of rat stromal cell derived factor-1 (SDF-1)1: SDF-1 alpha mRNA is selectively induced in rat model of myocardial infarction," *Inflammation*, 2001, 25:293-300.
Rosenzweig, "Cardiac cell therapy—mixed results from mixed cells," *N. Engl. J Med.*, 2006, 355:1274-1277.
Sanchez et al., "Contemplating the bright future of stem cell therapy for cardiovascular disease," *Nat. Clin. Pract. Cardiovasc. Med.*, 2006, 3 Suppl.(1):S138-S151.
Schachinger et al., "Intracoronary bone marrow-derived progenitor cells in acute myocardial infarction," *N. Engl. J. Med.*, 2006, 355:1210-1221.
Singla et al., "Transplantation of embryonic stem cells into the infarcted mouse heart: formation of multiple cell types," *J. Mol. Cell. Cardiol.*, 2006, 40:195-200.
Smith et al , "Inhibition of pluripotential embryonic stem cell differentiation by purified polypeptides," *Nature*, 1988, 336:688-690.
Srivastava and Ivey, "Potential of stem-cell-based therapies for heart disease," *Nature*, 2006, 441:1097-1099.
Srivastava, "Making or breaking the heart: from lineage determination to morphogenesis," *Cell*, 2006, 126:1037-1048.
Sugi and Lough, "Activin-A and FGF-2 mimic the inductive effects of anterior endoderm on terminal cardiac myogenesis in vitro," *Dev. Biol.*, 1995, 168:567-574.
Tada et al., "Characterization of mesendoderm: a diverging point of the definitive endoderm and mesoderm in embryonic stem cell differentiation culture," *Development*, 2005, 132:4363-4374.
Taniuchi et al., "Dizygotic twin sisters with myelokathexis: mechanism of its neutropenia," *Am. J. Hematol.*, 1999, 62:106-111.
Torella et al. "Cardiac stem cells regenerate the infarcted heart, restoring function and long-term survival in mice," *Circulation*, 2004, 110(17), Suppl III, 4 pages, (Abstract only—abstract on last page).
Vandervelde et al., "Signaling factors in stem cell-mediated repair of infarcted myocardium," *J. Mol. Cell Cardiol.*, 2005, 39:363-376.
Wobus et al., "Retinoic acid accelerates embryonic stem cell-derived cardiac differentiation and enhances development of ventricular cardiomyocytes," *J. Mol. Cell Cardiol.*, 1997, 29:1525-1539.
Wu et al., "Developmental origin of a bipotential myocardial and smooth muscle cell precursor in the mammalian heart," *Cell*, 2006, 127:1137-1150.
Yamaguchi et al., "flk-1, an flt-related receptor tyrosine kinase is an early marker for endothelial cell precursors," *Development*, 1993, 118:489-498.
Yamashita et al., "Differentiation and diversification of vascular cells from embryonic stem cells," *Int. J. Hematol.*, 2004, 80(6808):92-96.
Yamashita et al., "F1kl-positive cells derived from embryonic stem cells servie as vascular progenitors," *Nature*, Nov. 2, 2000, 408:92-96.
Yamashita et al., "Prospective identification of cardiac progenitors by a novel single cell-based cardiomyocyte induction," *FASEB Journal*, 2005, 19:1534-1536.
Yasunaga et al., "Induction and monitoring of definitive and visceral endoderm differentiation of mouse ES cells," *Nat. Biotechnol.*, 2005, 23:1542-1550.
Yuasa et al., "Transient inhibition of BMP signaling by Noggin induces cardiomyocyte differentiation of mouse embryonic stem cells," *Nat. Biotechnol.*, 2005, 23:607-611.
Yusuf et al, "Expression of chemokine receptor CXCR4 during chick embryo development," *Anat. Embryol. (Berl)*, 2005, 210:35-41.
Zaffran and Frasch, "Early signals in cardiac development," *Circ. Res.*, Sep. 20, 2002, 91(6):457-469.
Zaffran et al., "Cardioblast-intrinsic Tinman activity controls proper diversification and differentiation of myocardial cells in *Drosophila*," *Development*, 2006, 133:4073-4083.
Zhu et al., "Evidence that FGF receptor signaling is necessary for endoderm-regulated development of precardiac mesoderm," *Mech. Ageing Dev.*, 1999, 108:77-85.
Zou et al., "Function of the chemokine receptor CXCR4 in haematopoiesis and in cerebellar development," *Nature*, 1998, 393:595-599.
United States Office Action in U.S. Appl. No. 11/572,874, mailed Nov. 24, 2010, 12 pages.
United States Office Action in U.S. Appl. No. 11/572,874, mailed Apr. 29, 2010, 13 pages.
United States Office Action in U.S. Appl. No. 11/572,874, mailed Nov. 16, 2009, 6 pages.
United States Office Action in U.S. Appl. No. 11/572,874, mailed Mar. 23, 2009, 11 pages.
United States Office Action in U.S. Appl. No. 12/530,165, mailed May 25, 2012, 11 pages.
United States Office Action in U.S. Appl. No. 12/994,626, mailed Jul. 24, 2012, 20 pages.
United States Office Action in U.S. Appl. No. 12/994,626, mailed Feb. 28, 2013, 18 pages.
United States Office Action in U.S. Appl. No. 11/674,461, mailed Oct. 21, 2009, 17 pages.
United States Office Action in U.S. Appl. No. 11/674,461, mailed Jun. 8, 2010, 11 pages.
United States Office Action in U.S. Appl. No. 11/674,461, mailed Feb. 9, 2011, 11 pages.
Chinese Office Action in Chinese Application No. 200980118954, dated Aug. 31, 2012, 15 pages.
Extended European Search Report in European Application No. 09763198.0, dated Jun. 13, 2012, 11 pages.
European Office Action in European Application No. 05777528.0, dated Feb. 2, 1010, 6 pages.
European Office Action in European Application No. 05777528.0, dated Nov. 26, 2010, 5 pages.
European Office Action in European Application No. 10179541.7, dated Jun. 5, 2012, 5 pages.
Extended European Search Report in European Application No. 10179541.7, dated Nov. 24, 2010, 9 pages.
Extended European Search Report in European Application No. 08731697.2, dated Mar. 10, 2011, 8 pages.
International Search Report and Written Opinion in International Application No. PCT/US2009/044751, dated Feb. 17, 2010, 14 pages.
International Search Report and Written Opinion in International Application No. PCT/US2010/035616, dated Aug. 3, 2010, 13 pages.
International Preliminary Report on Patentability in International Application No. PCT/US2010/035616, dated Jul. 5, 2011, 10 pages.
International Preliminary Report Written on Patentability in PCT/US2008/056248, issued Sep. 8 2009, 6 pages.
International Search Report and Written Opinion of the International Searching Authority in PCT/US2008/056248, mailed Jun. 23, 2008, 11 pages.
International Preliminary Report on Patentability in International Application No. PCT/US2008/064895, mailed Dec. 9, 2010, 7 pages.
International Search Report and Written Opinion in Internatioanl Application No. PCT/US2008/064895, mailed Feb. 24, 2009, 13 pages.
International Preliminary Report on Patentability in International Application No. PCT/US2005/026800, mailed Apr. 26, 2007, 6 pages.
International Search Report and Written Opinion in International Application No. PCT/U52005/026800, Mar. 28, 2007, 12 pages.
International Search Report and Written Opinion in International Application No. PCT/US2009/044714, dated Feb. 25, 2010, 16 pages.
International Preliminary Report on Patentability in International Application No. PCT/US2009/044714, mailed Dec. 9, 2010, 9 pages.
Office Action in Mexico Application No. MX/a/2010/012998, dated Oct. 22, 2012, 6 pages.
Aicher et al., "Essential role of endothelial nitric oxide synthase for mobilization of stem and progenitor cells," Nature Medicine, 2003, 9:1370-1376.

(56) References Cited

OTHER PUBLICATIONS

Andree et al., "BMP-2 induces ectopic expression of cardiac lineage markers and interferes with somite formation in chicken embryos," *Mech. Dev.*, 1998, 70:119-131.

Anversa and Nadal-Ginard, "Myocyte renewal and ventricular remodelling," *Nature*, 2002, 415:240-243.

Arrell et al., "Proteomic analysis of pharmacologically perconditioned cardiomyocytes reveals novel phosphorylation of myosin light chain 1," *Circulation Research*, 2001, 89: 480-487.

Askari et al., "Effect of stromal-cell-derived factor 1 on stem-cell homing and tissue regeneration in ischaemic cardiomyopathy," *Mechanisms of Disease*, 2003, 362: 697-703.

Baddoo et al., "Characterization of Mesenchymal Stem Cells Isolated from Murine Bone Marrow by Negative Selection," *Journal of Cellular Biochemistry*, 2003, 89: 1235-1249.

Behfar et al., "Stem cell differentiation requires a paracrine pathway in the heart," *FASEB J.*, 2002, 16:1558-1566.

Behfar et al., "Newly Identified Cardiopoietic Stem Cell Population Recruited by TNF-α from Pluripotent Embryonic Cells," *Circulation*, 2004, 110(17):III-302, Abstract No. 1444.

Behfar et al., "Cardiopoietic programming of embryonic stem cells for tumor-free heart repair," *J. Exp. Med.*, 2007, 204(2):405-420.

Behfar and Terzic, "Derivation of a cardiopoietic population from human mesenchymal stem cells yields cardiac progeny," *Nat. Clin. Pract. Cardiovasc. Med.*, 2006, 3(Suppl 1):S78-S82.

Beltrami et al., "Evidence that human cardiac myocytes divide after myocardial infarction," *N. Engl. J. Med.*, 2001, 344:1750-1757.

Beltrami et al., "Adult Cardiac Stem Cells Are Multipotent and Support Myocardial Regeneration," *Cell*, 2003, 114:763-776.

Boheler et al., "Differentiation of Pluripotent Embryonic Stem Cells Into Cardiomyocytes," *Circ. Res.*, 2002, 91:189-201.

Bondue et al., "Mesp1 acts as a master regulator of multipotent cardiovascular progenitor specification," *Cell Stem Cell*, 2008, 3(1):69-84.

Britten et al., "Infarct remodeling after intracoronary progenitor cell treatment in patients with acute myocardial infarction (TOPCARE-AMI): Mechanistic insights from serial contrast-enhanced magnetic resonance imaging," *Circulation*, 2003, pp. 2212-2218.

Caplice et al., "Cell therapy for cardiovascular disease: what cells, what diseases and for whom?" *Nat. Clin. Pract. Cardiovasc. Med.*, 2005, 2:37-43.

Chien et al., "ES Cells to the Rescue," *Science*, 2004, 306:239-240.

Daniels et al., "Imatinib mesylate inhibits the profibrogenic activity of TGF-β and prevents bleomycin mediated lung fibrosis," *J Clin invest*, 2004, 114: 1308-1316.

Dawn and Bolli, "Bone marrow cells for cardiac regeneration: the quest for the protagonist continues," *Cardiovasc. Res.*, 2005, 65(2):293-295.

Dawn et al., "Cardiac stem cells delivered intravascularly traverse the vessel barrier, regenerate infracted myocardium, and improve cardiac function," *PNAS*, 2005, 102(10): 3766-3771.

Dimmeler et al., "Unchain my heart: the scientific foundations of cardiac repair," *J. Clin. Invest.*, 2005, 115(3):572-583.

Drukker et al., "Characterization of the expression of MHC proteins in human embryonic stem cells," *PNAS*, 2002, 99(15): 9864-9869.

Edgeworth et al., "Ionomycin-regulated phosphorylation of the myeloid calcium-binding protein p14," *Nature*, 1989, 342:189-192.

Erdo et al., "Host-dependent tumorigenesis of embryonic stem cell transplanation in experimental stroke," J. Cereb. Blood Flow Metab., 2003, 23:780-785.

Fernández-Avilés et al., "Experimental and Clinical Regenerative Capability of Human Bone Marrow Cells After Myocardial Infarction," *Circ. Res.*, 2004, 95:742-748.

Fijnvandraat et al., "Cardiomyocytes purified from differentiated embryonic stem cells exhibit characteristics of early chamber myocardium," *J. Mol. Cell. Cardiol.*, 2003, 35(12):1461-1472.

Foley and Mercola, "Heart Induction: Embryology to Cardiomyocyte Regeneration," *Trends Cardiovasc. Med.*, 2004, 14:121-125.

Fraidenraich et al., "Rescue of Cardiac Defects in id Knockout Embryos by Injection of Embryonic Stem Cells," *Science*, 2004, 306:247-252.

Frandrich et al., "Preimplantation-stage stem cells induce long-term allogeneic graft acceptance without supplementary host conditioning," *Nature Medicine*, 2002, 8(2): 171-178.

Fukuda, "Development of Regenerative Cardiomyocytes from Mesenchymal Stem Cells for Cardiovascular Tissue Engineering," *Artificial Organs*, 2001, 25(3):187-193.

Fukuda, "Molecular characterization of regenerated cardiomyocytes derived from adult mesenchymal stem cells," *Congenital Anomalies*, 2002, 42:1-9.

Gepstein, "Derivation and Potential Applications of Human Embryonic Stem Cells," *Circ. Res.*, 2002, 91:866-876.

Gharandaghi et al., "Mass spectrometric identification of proteins from silver-stained polyacrylamide gel: A method for the removal of silver ions to enhance sensitiviry," *Electrophoresis*, 1999, 20: 601-605.

Ghosh et al., "Physical interaction between TBX5 and MEF2C is required for early heart development," *Molecular and Cellular Biology*, 2009, 29(8): 2205-2218.

Gnecchi et al., "Paracrine action accounts for marked protection of ischemic heart by Akt-modified mesenchymal stem cells," *Nat. Med.*, 2005, 11(4):367-368.

He et al., "Human Embryonic Stem Cells Develop Into Multiple Types of Cardiac Myocytes: Action Potential Characterization," *Circ. Res.*, 2003, 93:32-39.

Hodgson et al., "Cellular remodeling in heart failure disrupts $K_{ATP}$ channel-dependent stress tolerance," *EMBO J.*, 2003, 22(8):1732-1742.

Hodgson et al., "Stable benefit of embryonic stem cell therapy in myocardial infarction," *Am. J. Physiol. Heart Circ. Physiol.*, 2004, 287:H471-H479.

Itescu et al., "New directions in strategies using cell therapy for heart disease," *J. Mol. Med.*, 2003, 82:288-296.

Jiang et al., "Common Role for Each of the cGATA-4/5/6 Genes in the Regulation of Cardiac Morphogenesis," *Dev. Genet.*, 1998, 22:263-277.

Kane et al., "ATP-Sensitive K+ challel knockout compromises the metabolic benefit of exercise training, resulting in cardiac deficits," *Diabetes*, 2004, 53: 169-175.

Kehat et al., "Electromechanical integration of cardiomyocytes derived from human embryonic stem cells," *Nat. Biotechnol.*, 2004, 22(10):1282-1289.

Koh et al., "Co-culture of human CD34+ cells with mesenchymal stem cells increases the survival of CD34+ cells against the 5-aza-deoxycytidine- or trichostatin A-induced cell death," *Biochem. Biophys. Res. Commun.*, 2005, 329:1039-1045.

Kucia et al., "Cells Expressing Early Cardiac Markers Reside in the Bone Marrow and Are Mobilized Into the Peripheral Blood After Myocardial Infarction," *Circ. Res.*, 2004, 95:1191-1199.

Kwon et al., "An Essential Role of N-Terminal Arginylation in Cardiovascular Development," *Science*, 2002, 297:96-99.

Laugwitz et al., "Postnatal isl1+ cardioblasts enter fully differentiated cardiomyocyte lineages," *Nature*, 2005, 433:647-653.

Levenberg et al., "Endothelial cells derived from human embryonic stem cells," *PNAS*, 2002, 99: 4391-4396.

Lila et al., "Human leukocyte antigen-G expression after heart transplantation is assocaited with a reduced indicence of rejection," *Circulation*, 2002, 105: 1949-1954.

Lin et al., "Control of mouse cardiac morphogenesis and myogenesis by tanscription factor MEF2C," *Science*, 1997, 276: 1404-1407.

Locksley et al., "The TNG and TNF receptor superfamilies: Integrating mammalian biology," *Cell*, 2001, 104:487-501.

Lutz et al., "Nucleoside Diphosphate Kinase-Mediated Activation of Heterotrimeric G Proteins," *Meth. Enzymol.*, 2004, 390:403-418.

Maltsev et al., "Cardiomyocytes differentiated in vitro from embryonic stem cells developmentally express cardiac-specific genes and ionic currents," *Circulation Research*, 1994, 75: 233-244.

Mangi et al., "Mesenchymal stem cells modified with Akt prevent remodeling and restore performance of infarcted hearts," *Nature Medicine*, 2003, 9: 1195-1201.

(56) References Cited

OTHER PUBLICATIONS

Menaschéet al., "Autologous Skeletal Myoblast Transplantation for Severe Postinfarction Left Ventricular Dysfunction," *J. Am. Coll. Cardiol.*, 2003, 41(7):1078-1083.

Menasché, "Embryonic stem cells pace the heart," *Nat. Biotechnol.*, 2004, 22(10):1237-1238.

Méry et al., "Commitment of embryonic stem cells toward a caridac lineage: molecular mechanisms and evidence for a promising therapeutic approach for heart failure," *J. Muscle Res. Cell Motility*, 2003, 24:269-274.

Meyer et al., "A fluorescent reporter gene as a marker for ventricular specification in ES-derived cardiac cells," 2000, *FEBS Letters*, 478:151-158.

Min et al., "Long-term improvement of cardiac function in rats after infarction by transplantation of embryonic stem cells," *J. Thorac. Cardiovasc. Surg.*, 2003, 125(2):361-369.

Min et al., "Transplantation of embryonic stem cells improves cardiac function in postinfarcted rats," *J. Appl. Physiol.*, 2002, 92:288-296.

Mohri et al., "Expression of cofilin isoforms during development of mouse striated muscles," *J. Muscle Res. Cell Motil.*, 2000, 21:49-57.

Mummery et al., "Differentiation of Human Embryonic Stem Cells to Cardiomyocytes. Role of Coculture With Visceral Endoderm-Like Cells," *Circulation*, 2003, 107:2733-2740.

Murry et al., "Cellular Therapies for Myocardial Infarct Repair," *Cold Spring Harbor Symp. Quant. Biol.*, 2002, 67:519-526.

Murry et al., "Hematopoietic stem cells do not transdifferentiate into cardiac myocytes in myocardial infarcts," *Nature*, 2004, 428:664-668.

Nakano et al., "Tumor necrosis factor-alpha confers resistance to hypoxia injury in the adult mammalian cardiac myocytes," *Circulation*, 1998, 97: 1392-1400.

Nichols et al., "Formation of pluripotent stem cells in the mammalian embryo depends on the POU transcription factor OCt4," *Cell*, 95: 379-391.

Nir et al., "Human embryonic stem cells for cardiovascular repair," *Cardiovasc. Res.*, 2003, 58:313-323.

Nygren et al., "Bone marrow-derived hematopoietic cells generate cardiomyocytes at a low frequency through cell fusion, but not transdifferentiation," *Nat. Med.*, 2004, 10(5):494-501.

Obinata et al., "Low Molecular-weight G-actin Binding Proteins Involved in the Regulation of Actin Assembly during Myofibrillogenesis," *Cell Struct. Funct.*, 1997, 22:181-189.

O'Cochlain et al., "Transgenic overexpression of human *DMPK* accumulates into hypertrophic cardiomyopathy, myotonic myopathy and hypotension traits of myotonic dystrophy," *Human Molecular Genetics*, 2004, 13(20): 2505-2518.

Oh et al., "Cardiac progenitor cells from adult myocardium: Homing, differentiation, and fusion after infarction," *Proc. Natl. Acad. Sci. USA*, 2003, 100(21):12313-12318.

Olson and Schneider, "Sizing up the heart: Development redux in disease," *Genes Dev.*, 2003, 17:1937-1956.

Orlic et al., "Stem Cells for Myocardial Regeneration," *Circ. Res.*, 2002, 91:1092-1102.

Orlic et al., "Bone marrow cells regenerate infarcted myocardium," *Nature*, 2001, 410:701-705.

Perez-Terzic et al., "Directed inhibition of nuclear import in cellular hypertrophy," *J. Biological Chemistry*, 2001, 276(23): 20566-20571.

Perez-Terzic et al., "Structural Adaptation of the Nuclear Pore Complex in Stem Cell-Derived Cardiomyocytes," *Circ. Res.*, 2003, 92:444-452.

Perin et al., "Improved Exercise Capacity and Ischemia 6 and 12 Months After Transendocardial Injection of Autologous Bone Marrow Mononuclear Cells for Ischemic Cardiomyopathy," *Circulation*, 2004, 110(suppl II):II-213-II-218.

Pittenger and Martin, "Mesenchymal Stem Cells and Their Potential as Cardiac Therapeutics," *Circ. Res.*, 2004, 95:9-20.

Rajasingh et al., "STAT3-dependent mouse embryonic stem cell differentiation into cardiomyocytes analysis of molecular signaling and therapeutic efficacy of cardiomyocyte precommitted mES transplantation in a mouse model of myocardial infarction," *Circulation Research*, 2007, 101(9): 910-918.

Rangappa et al., "Cardiomyocyte-mediated contact programs human mesenchymal stem cells to express cardiogenic phenotype," *J. Thorac. Cardiovasc. Surg.*, 2003, 126:124-132.

Rudy-Reil and Lough, "Avian Precardiac Endoderm-Mesoderm Induces Cardiac Myocyte Differentiation in Murine Embryonic Stem Cells," *Circ. Res.*, 2004, 94:e107-e116.

Sachinidis et al., "Cardiac specific differentiation of mouse embryonic stem cells," *Cardiovasc Res.*, 2003, 58:278-291.

Sadygov et al., "Large-scale database searching using tandem mass spectra: Looking up the answer in the back of the book," *Nature*, 2004, 1(3): 195-202.

Sauer et al., "Involvement of reactive oxygen species in cardiotrophin-1-induced roliferation of cardiomyocytes differentiated from murine embryonic stem cells," *Exp. Cell. Res.*, 2004, 294: 313-324.

Schächinger et al., "Transplantation of Progenitor Cells and Regeneration Enhancement in Acute Myocardial Infarction. Final One-Year Results of the TOPCARE-AMI Trial," *J. Am. Coll. Cardiol.*, 2004, 44(8):1690-1699.

Seino and Mike, "Physiological and pathophysiological roles of ATP-sensitive K+ Channels," *Biophysics & Molecular Biology*, 2003, 81: 133-176.

Shachauf et al., "MYC inactivation uncovers pluripotent differentiation and tumour dormancy in hepatocellular cancer," *Nature*, 2004, 431: 1112-1117.

Shevchenko et al., "Mass spectrometric sequencing of proteins from silver-stained polyacrylamide gels," *Anal. Chem*, 1996, 68: 850-858.

Shim et al., "Ex vivo differentiation of human adult bone marrow stem cells into cardiomyocyte-like cells," *Biochem. Biomes. Res. Commun.*, 2004, 324:481-488.

Sivasubramanian et al., "Left ventricular remodeling in transgenic mice with cardiac restricted overexpression of tumor necrosis factor," *Circulation*, 2001, 104: 826-831.

Smart et al., "A differential screen for putative targets of the bHLH transcription factor *Hand1* in cardiac morphogenesis," *Gene Expr. Patterns*, 2002, 2:61-67.

Solloway and Harvey, "Molecular pathways in myocardial development: a stem cell perspective," *Cardiovasc. Res.*, 2003, 58:264-277.

Srivasta et al., "A genetic blueprint for cardiac development," *Nature*, 2000, 407: 221-226.

Takeda et al., "Can the life span of human marrow stromal cells be prolonged by bmi-1, E6, E7, and/or telomerase without affecting cardiomyogenic differentiation?" *J. Gene Med.*, 2004, 6(8):833-845.

Terzic et al., "Structural Adaptation of the Nuclear Pore Complex in Stem Cell-Derived Cardiomyocytes," *Circ. Res.*, 2003, 92:444-452.

Thompson et al., "Comparison of Intracardiac Cell Transplantation: Autologous Skeletal Myoblasts Versus Bone Marrow Cells," *Circulation*, 2003, 108[suppl II]:II-264-II-271.

Thomson et al., "Embryonic stem cell lines derived from human blastocysts," *Science*, 1998, 282:1145-1147.

Toma et al., "Human Mesenchymal stem Cells Differentiate to a Cardiomyocyte Phenotype in the Adult Murine Heart," *Circulation*, 2002, 105:93-98.

Tomita et al., "Autologous Transplantation of Bone Marrow Cells Improves Damaged Heart Function," *Circulation*, 1999, 100(suppl. II):II-247-II-256.

Towbin and Bowles, "The failing heart," *Nature*, 2002, 415:227-233.

Tsuji, H., et al., "Amniotic Membrane-Derived Stem Cell, Supplemental materials, Figure Legends for Supplemental Material," 205260-R3, pp. 1-26 (2009).

Tsuji, H., et al., "Xenografted Human Amniotic Membrane-Derived Mesenchymal Stem Cells Are Immunologically Tolerated and Transdifferentiated Into Cardiomyocytes," Circulation Research, 106:1613-1623 (2010).

Vassilopoulos et al., "Transplanted bone marrow regenerates liver by cell fusion," *Nature*, 2003, 422: 901-904.

Wang et al., "Cell fusion is the principal source of bone-marrow-derived hepatocytes," *Nature*, 2003, 422: 897-901.

(56) References Cited

OTHER PUBLICATIONS

Wojakowski et al., "Mobilization of CD34/CXCR4+, CD34/CD117+, c-met+ stem cells and mononuclear cells expressing early cardiac, muscle, and endothelial markers into peripheral blood in patients with acute myocardial infarction," *Circ.*, 2004, 110: 3213-3220.

Wollert and Drexler, "Mesenchymal stem cells for myocardial infarction: Promises and Pitfalls," *Circ. Res.*, 2005, 96:151-163.

Wollert and Drexler, "Clinical Applications of Stem Cells for the Heart," *Circ. Res.*, 2005, 96:151-163.

Wollert et al., "Intracoronary autologous bone-marrow cell transfer after myocardial infarction: the BOOST randomised controlled clinical trial," *Lancet*, 2004, 364:141-148.

Wu et al., "Small molecules that induce cardiomyogenesis in embryonic stem cells," *J. Am. Chem. Soc.*, 2004, 126(6): 1590-1591.

Xaymardan et al., Platelet-Derived Growth Factor-AB Promotes the Generation of Adult Bone Marrow-Derived Cardiac Myocytes, *Circ. Res.*, 2004, 94:e39-e45.

Xin et al., "Oestrogen protects FKBP12.6 null mice from cardiac hypertrophy," *Nature*, 2002, 416:334-338.

Xu et al., "Mesenchymal Stem Cells from Adult Human Bone Marrow Differentiate into a Cardiomyocyte Phenotype In Vitro," *Exp. Biol. Med.*, 2004, 229:623-631.

Yang et al., "VEGF enhances functional improvement of postinfarcted hearts by transplantation of ESC-differentiated cells," *J. Appl. Physiol.*, 2002, 93: 1140-1151.

Yoon et al., "Myocardial regeneration with bone-marrow-derived stem cells," *Biol. Cell*, 2005, 97:253-263.

Zhao et al., "Human amniotic mesenchymal cells have some characteristics of cardiomyocytes," *Transplantation*, 2005, 79: 528-535.

Zingman et al., Tandem function of nucleotide binding domains confers competence to sultonylurea receptor in gating ATP-sensitive K+ channels, *J. Biol. Chem.*, 2002, 277(16): 14206-14210.

Zingman et al., "Kir6.2 is required for adaptation to stress," PNAS, 90(20): 13278-13283.

United States Office Action in U.S. Appl. No. 13/321,100, mailed Jul. 12, 2013, 14 pages.

Levsky et al. (2002) Science, vol. 297, pp. 836-840.

"AMOS 5 Correlation" http://www.math.ntua.gr/-fouskakis/SS/correlation.pdf (Jul. 7, 2013).

* cited by examiner

SEQUENCE LISTING

```
<160> NUMBER OF SEQ ID NOS: 8

<210> SEQ ID NO 1
<211> LENGTH: 28
<212> TYPE: DNA
<213> ORGANISM: Artificial Sequence
<220> FEATURE:
<223> OTHER INFORMATION: Oligonucleotide

<400> SEQUENCE: 1
tgcagaaggc agtggagctg gacaagcc                                          28

<210> SEQ ID NO 2
<211> LENGTH: 27
<212> TYPE: DNA
<213> ORGANISM: Artificial Sequence
<220> FEATURE:
<223> OTHER INFORMATION: Oligonucleotide

<400> SEQUENCE: 2
ttgcacttgt agcgacggtt ctggaac                                           27

<210> SEQ ID NO 3
<211> LENGTH: 25
<212> TYPE: DNA
<213> ORGANISM: Artificial Sequence
<220> FEATURE:
<223> OTHER INFORMATION: Oligonucleotide

<400> SEQUENCE: 3
agatacccac aacacaccac gcgcc                                             25

<210> SEQ ID NO 4
<211> LENGTH: 25
<212> TYPE: DNA
<213> ORGANISM: Artificial Sequence
<220> FEATURE:
<223> OTHER INFORMATION: Oligonucleotide

<400> SEQUENCE: 4
atccttcaga gactcgcatg cgctt                                             25

<210> SEQ ID NO 5
<211> LENGTH: 25
<212> TYPE: DNA
<213> ORGANISM: Artificial Sequence
<220> FEATURE:
<223> OTHER INFORMATION: Oligonucleotide

<400> SEQUENCE: 5
ggaattcaag atgaacggca tcaac                                             25
```

```
<210> SEQ ID NO 6
<211> LENGTH: 28
<212> TYPE: DNA
<213> ORGANISM: Artificial Sequence
<220> FEATURE:
<223> OTHER INFORMATION: Oligonucleotide

<400> SEQUENCE: 6
tgaattctca acctgctggc gtcttaga                                            28

<210> SEQ ID NO 7
<211> LENGTH: 26
<212> TYPE: DNA
<213> ORGANISM: Artificial Sequence
<220> FEATURE:
<223> OTHER INFORMATION: Oligonucleotide

<400> SEQUENCE: 7
gccaaaacac caacctgtcc aagttc                                              26

<210> SEQ ID NO 8
<211> LENGTH: 22
<212> TYPE: DNA
<213> ORGANISM: Artificial Sequence
<220> FEATURE:
<223> OTHER INFORMATION: Oligonucleotide

<400> SEQUENCE: 8
ctgctggaga ggttattcct cg                                                  22
```

TREATING CARDIOVASCULAR TISSUE

CROSS-REFERENCE TO RELATED APPLICATIONS

This application is a divisional of U.S. application Ser. No. 11/572,874, filed Dec. 26, 2007, which is a National Stage application under 35 U.S.C. §371 and claims benefit under 35 U.S.C. §119(a) of International Application No. PCT/US2005/026800 having an International Filing Date of Jul. 29, 2005, which claims the benefit of priority under 35 U.S.C. §119(e) of U.S. Application No. 60/680,775, filed May 12, 2005 and U.S. Application No. 60/592,871, filed Jul. 30, 2004. The disclosures of the prior applications are incorporated by reference in their entirety.

BACKGROUND

1. Technical Field

This document relates to methods and materials involved in treating cardiovascular tissue with, for example, stem cells.

2. Background Information

Myocardial injury leads to cardiomyocyte loss, ventricular remodeling and consequent impairment of myocardial function. Unfortunately, the mitotic capacity of cardiomyocytes is too limited to support adequate myocardial regeneration. In addition, current therapeutic modalities attenuate disease progression without contributing significantly to myocardial repair.

Pluripotent cells such as embryonic stem cells can proliferate indefinitely in vitro and can differentiate, in vitro, into cells that recapitulate the cardiac phenotype by expressing characteristic cardiac markers and demonstrating functional excitation-contraction coupling. When transplanted into injured hearts, embryonic stem cells can generate cardiomyocytes that repopulate regions of dysfunctional myocardium and improve contractile performance. Pluripotent stem cells, however, can form tumor cells once removed from the native hematopoietic environment.

SUMMARY

This document provides methods and materials related to treating cardiovascular tissue (e.g., heart tissue or vascular tissue). For example, this document provides stem cells, compositions containing stem cells, methods for obtaining stem cells, compositions for generating stem cells expressing particular markers, and methods for repairing cardiovascular tissue. The stem cells and compositions containing stem cells provided herein can be used to repair cardiovascular tissue. Such stem cells can allow clinicians to treat, for example, myocardial injury since the stem cells can have the ability to differentiate into cardiomyocytes. In some cases, such stem cells and compositions containing stem cells can be used to repair cardiovascular tissue without producing tumors within the tissue. The compositions provided herein for generating stem cells can allow medical professionals to produce large amounts of stem cells that can express particular markers and can be used to repair cardiovascular tissue.

In general, one aspect of this document features a method for treating heart or vascular tissue. The method includes administering stem cells to the heart or vascular tissue under conditions wherein the stem cells do not develop tumor cells in the heart or vascular tissue. The stem cells can be injected into the heart of a mammal (e.g., a human). The stem cells can be embryonic stem cells or stem cells expressing one or more of the polypeptides listed in the third column of Table 1. The stem cells can be injected in an amount less than about 1500 stem cells per mg of heart or vascular tissue. The heart or vascular tissue can be tissue that was contacted with TNF-α, TGF-β, or γ-interferon. The method can include contacting the heart or vascular tissue with TNF-α, TGF-β, or γ-interferon. This contacting step can occur before, during, or after the stem cells are administered.

Embryonic stem cells can be administered to heart tissue or vascular tissue such that tumors do not develop. For example, less than 1000 embryonic stem cells per 1 mg of tissue can be injected into a mammal (e.g., human, primate, horse, dog, cat, pig, cow, or rodent). In some embodiments, about 50 to 1500 cells (e.g., 100 to 1500, 200 to 1500, 500 to 1500, 200 to 1000, or 500 to 1000 cells) per 1 mg of heart tissue can be administered to a mammal without a risk of developing tumors. When injecting embryonic stem cells into a mouse, whose heart weighs about 300 mg, $3 \times 10^5$ cells can be administered. Injecting 3300 cells per 1 mg of heart tissue can result in a 15 percent tumor risk, while injecting 10,000 cells per 1 mg of heart tissue can result in a 72 percent tumor risk.

In another embodiment, this document features a stem cell that expresses (a) at least one polypeptide selected from the group consisting of Oct4; DEK; BRCA1; Ect2; and MYC; (b) at least one polypeptide selected from the group consisting of Fosb; NRAP; MEF2A; Furin; TGFβ1; fibronectin receptor a; discoidin domain receptor 1; bag2; cystein rich protein; CUGBP2; NDRG4; CBP/p300 inhibitory protein 1; interferon inducible protein 1; tropomyosin 1, alpha; Rho GTPase activating protein 1; carboxypeptidase D; profilin 2; transforming growth factor beta 1 induced transcript 1; tropomyosin 1, alpha; growth hormone receptor; vinculin; adenylate cyclase 6; S100 calcium binding protein A1; tropomyosin 2, beta; retinol binding protein 1, cellular; Moesin; matrix metalloproteinase 2; secreted acidic cysteine rich glycoprotein; mannosidase 1, alpha; lectin, galactose binding, soluble 1; S100 calcium binding protein A6 (calcyclin); epoxide hydrolase 1, microsomal; pleiomorphic adenoma gene-like 1; insulin-like growth factor 2; tubby like protein 4; prion protein; FK506 binding protein 10; cyclin D2; reticulocalbin 3, EF-hand calcium binding domain; selenoprotein M; cyclin-dependent kinase inhibitor 1A (P21); caldesmon 1; integrin beta 1 (fibronectin receptor beta); transcobalamin 2; annexin A2; cyclin-dependent kinase inhibitor 1A (P21); thrombospondin 1; monocyte to macrophage differentiation-associated; AXL receptor tyrosine kinase; annexin A5; muscleblind-like 2; annexin A1; procollagen, type IV, alpha 1; calpain 2; epithelial membrane protein 1; protease, serine, 11; tropomyosin 2, beta; lectin, galactose binding, soluble 9; and annexin A3; and (c) at least one polypeptide selected from the group consisting of integral membrane protein 2A; insulin-like growth factor binding protein 4; thymus cell antigen 1, theta; selenoprotein P, plasma, 1; glycoprotein 38; epidermal growth factor receptor pathway substrate 8; heat shock protein 1A; cellular retinoic acid binding protein I; and placenta-specific 8. The stem cell can two, three, four, or more of the polypeptides listed in each group. The stem cell can express the polypeptides listed in the third column of Table 1. In another embodiment, this document features progeny of these stem cells.

In another aspect, the invention features stem cells, wherein the stem cells exhibit nuclear translocation of cardiac transcription factors such as NKX2.5, Mes2C, and GATA4; and wherein the stem cells do not comprise sarcomeric proteins such as Annexin A6, Connective Tissue Growth Factor, Smad6, Na+ channel, L-Type $Ca^{2+}$ channel, $Ca^{2+}$ ATPase, MLC2V, MLC2a, α-MHC, α-actin, α-actinin, Troponin T2, or Titin.

In another embodiment, this document features a composition (i.e., a cardiogenic cocktail) containing TGF-β1; TGF-β2; BMP-1; BMP-2; BMP-5; BMP-6; FGF-4; FGF-5; FGF-12; FGF-13; FGF-15; FGF-20; leukemia inhibitory factor; VEGF-C; insulin growth factor-1; and interleukin 6. The cardiogenic cocktail can contain caspase-4; chemokine ligand 1; chemokine ligand 2; chemokine ligand 5; chemokine ligand 7; chemokine ligand 11; chemokine ligand 20; haptoglobin; colony stimulating factor-1; lectin; cholesterol 25-hydroxylase; syntaxin-8; syntaxin-11; ceruloplasmin; complement component 1; complement component 3; platelet derived growth factor; integrin alpha 6; lysosomal acid lipase 1; β-2 microglobulin; ubiquitin; macrophage migration inhibitory factor; retinoic acid; cofilin; cyclophillin A; FKBP12; NDPK; profilin 1; cystatin C; calcyclin, or any combination thereof. The cardiogenic cocktail, upon exposure to embryonic stem cells, can causes the embryonic stem cells to lose their tumorigenicity. The cardiogenic cocktail, upon exposure to embryonic stem cells, can causes the embryonic stem cells to commit to differentiating into cardiomyocytes.

In another embodiment, this document features a method of obtaining stem cells (e.g., cardiopoietic stem cells). The method includes contacting embryonic stem cells with a cardiogenic cocktail. The stem cells can express one or more of the polypeptides listed in the third column of Table 1. The method can include isolating cardiopoietic stem cells from embryonic stem cells or cardiomyocytes.

In another embodiment, this document features a method for determining whether or not cells are stem cells. The method includes determining whether or not the cells express (a) at least one polypeptide selected from the group consisting of Oct4; DEK; BRCA1; Ect2; and MYC; (b) at least one polypeptide selected from the group consisting of Fosb; NRAP; MEF2A; Furin; TGFβ1; fibronectin receptor a; discoidin domain receptor 1; bag2; cystein rich protein; CUGBP2; NDRG4; CBP/p300 inhibitory protein 1; interferon inducible protein 1; tropomyosin 1, alpha; Rho GTPase activating protein 1; carboxypeptidase D; profilin 2; transforming growth factor beta 1 induced transcript 1; tropomyosin 1, alpha; growth hormone receptor; vinculin; adenylate cyclase 6; S100 calcium binding protein A1; tropomyosin 2, beta; retinol binding protein 1, cellular; Moesin; matrix metalloproteinase 2; secreted acidic cysteine rich glycoprotein; mannosidase 1, alpha; lectin, galactose binding, soluble 1; S100 calcium binding protein A6 (calcyclin); epoxide hydrolase 1, microsomal; pleiomorphic adenoma gene-like 1; insulin-like growth factor 2; tubby like protein 4; prion protein; FK506 binding protein 10; cyclin D2; reticulocalbin 3, EF-hand calcium binding domain; selenoprotein M; cyclin-dependent kinase inhibitor 1A (P21); caldesmon 1; integrin beta 1 (fibronectin receptor beta); transcobalamin 2; annexin A2; cyclin-dependent kinase inhibitor 1A (P21); thrombospondin 1; monocyte to macrophage differentiation-associated; AXL receptor tyrosine kinase; annexin A5; muscleblind-like 2; annexin A1; procollagen, type IV, alpha 1; calpain 2; epithelial membrane protein 1; protease, serine, 11; tropomyosin 2, beta; lectin, galactose binding, soluble 9; and annexin A3; and (c) at least one polypeptide selected from the group consisting of integral membrane protein 2A; insulin-like growth factor binding protein 4; thymus cell antigen 1, theta; selenoprotein P, plasma, 1; glycoprotein 38; epidermal growth factor receptor pathway substrate 8; heat shock protein 1A; cellular retinoic acid binding protein I; and placenta-specific 8.

In another embodiment, this document features a method of making a cardiogenic cocktail. The method includes (a) obtaining ventral endodermal or ventral endodermal-like cells; (b) culturing the cells in medium, thereby generating conditioned culture medium; and (c) harvesting the conditioned culture medium, thereby obtaining a cardiogenic cocktail. The method can include adding one or more of the following components: IGF-1, IL-6, FGF-4, TGF-β, BMP, LIF, and hα-thrombin. The embryo from which the ventral endodermal cells are obtained can be TNF-α-stimulated. The ventral endodermal-like cells can be embryonal carcinoma cells.

In another embodiment, this document features a composition containing cells where at least 5 percent (e.g., at least 10, 15, 20, 25, 30, 40, 50, 60, 70, 80, 90, 95, or 99 percent) of the cells of the composition are stem cells that express (a) at least one polypeptide selected from the group consisting of Oct4; DEK; BRCA1; Ect2; and MYC; (b) at least one polypeptide selected from the group consisting of Fosb; NRAP; MEF2A; Furin; TGFβ1; fibronectin receptor a; discoidin domain receptor 1; bag2; cystein rich protein; CUGBP2; NDRG4; CBP/p300 inhibitory protein 1; interferon inducible protein 1; tropomyosin 1, alpha; Rho GTPase activating protein 1; carboxypeptidase D; profilin 2; transforming growth factor beta 1 induced transcript 1; tropomyosin 1, alpha; growth hormone receptor; vinculin; adenylate cyclase 6; S100 calcium binding protein A1; tropomyosin 2, beta; retinol binding protein 1, cellular; Moesin; matrix metalloproteinase 2; secreted acidic cysteine rich glycoprotein; mannosidase 1, alpha; lectin, galactose binding, soluble 1; S100 calcium binding protein A6 (calcyclin); epoxide hydrolase 1, microsomal; pleiomorphic adenoma gene-like 1; insulin-like growth factor 2; tubby like protein 4; prion protein; FK506 binding protein 10; cyclin D2; reticulocalbin 3, EF-hand calcium binding domain; selenoprotein M; cyclin-dependent kinase inhibitor 1A (P21); caldesmon 1; integrin beta 1 (fibronectin receptor beta); transcobalamin 2; annexin A2; cyclin-dependent kinase inhibitor 1A (P21); thrombospondin 1; monocyte to macrophage differentiation-associated; AXL receptor tyrosine kinase; annexin A5; muscleblind-like 2; annexin A1; procollagen, type IV, alpha 1; calpain 2; epithelial membrane protein 1; protease, serine, 11; tropomyosin 2, beta; lectin, galactose binding, soluble 9; and annexin A3; and (c) at least one polypeptide selected from the group consisting of integral membrane protein 2A; insulin-like growth factor binding protein 4; thymus cell antigen 1, theta; selenoprotein P, plasma, 1; glycoprotein 38; epidermal growth factor receptor pathway substrate 8; heat shock protein 1A; cellular retinoic acid binding protein I; and placenta-specific 8.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

In FIG. 2A, arrowheads indicate the location of Q-waves on electrocardiography. In FIG. 2B, arrowheads indicate sites of stem cell injection at the base, mid-ventricle and apex in the peri-infarct zone. Inset in FIG. 2B shows injection of stem cells into infarcted heart.

In FIG. 4B-4C, asterisks indicate significant difference in comparisons between the stem cell-treated and sham-treated groups.

DETAILED DESCRIPTION

Figure 1:
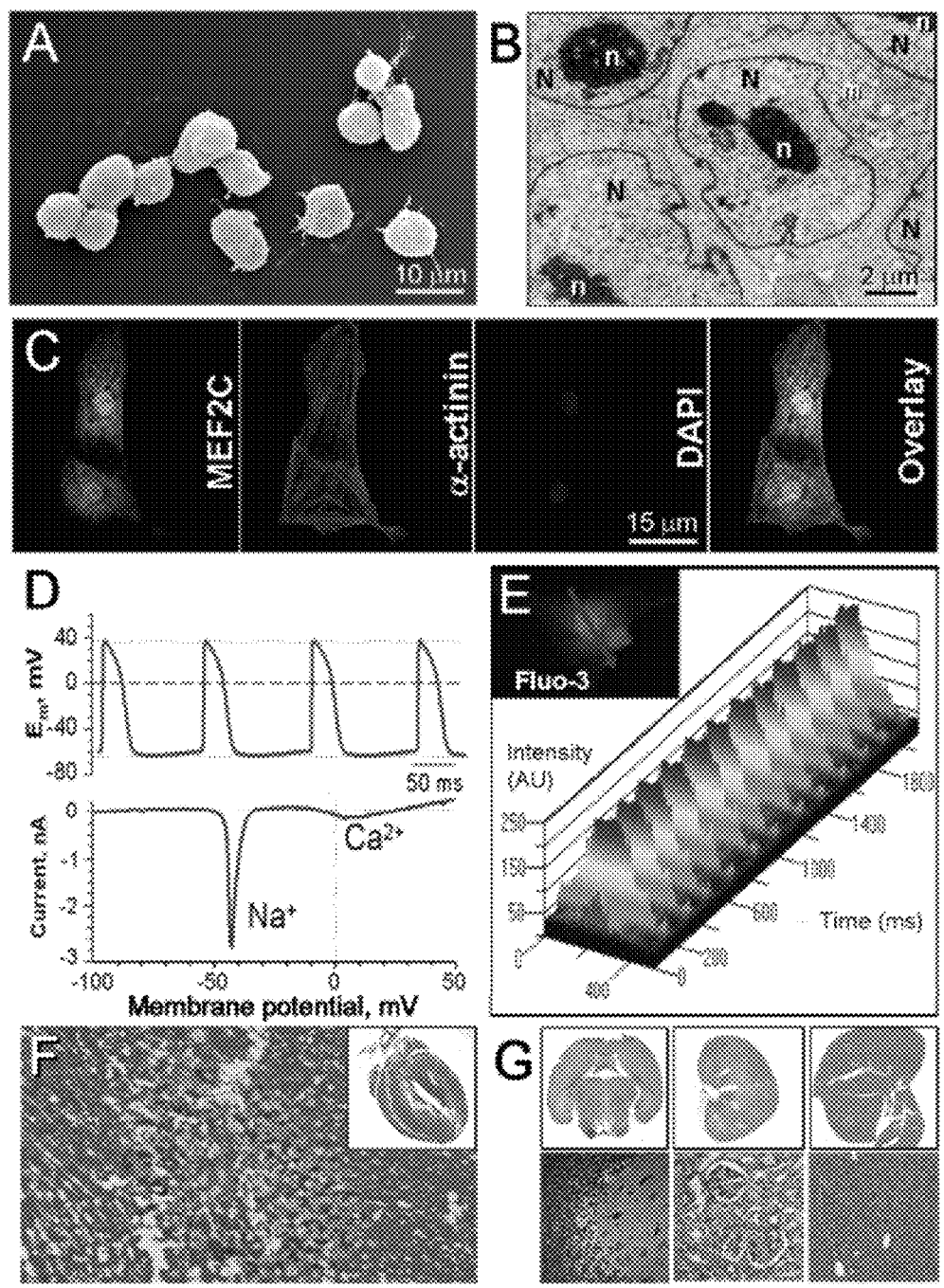
FIG. 1A and FIG. 1B are photographs using field emission scanning (A) and transmission (B) electron microscopy of undifferentiated CGR8 embryonic stem cells in culture.
FIG. 1C is a photograph of DAPI-stained cardiomyocytes derived in vitro from the CGR8 stem cell colony.
FIG. 1D (upper) is a graph showing that stem cell-derived cardiomyocytes exhibit action potential activity under current-clamp mode, while FIG. 1D (lower) is a graph showing that the current-voltage relationship was obtained under voltage-clamp mode in response to a ramp stimulus (rate of 1.2 V/s).
FIG. 1E shows calcium transients probed by Fluo3-assisted laser confocal microscopy from a stem cell-derived cardiomyocyte (inset), and recorded at 35±2° C.
FIG. 1F is a photograph showing local retention of CGR8 stem cells following intramyocardial delivery into mouse heart (inset), and cryosection (at 40× magnification) of myocardium with an overlay of fluorescing stem cells.
FIG. 1G is a photograph showing the lack of stem cell dispersion into non-cardiac tissues with absence of fluorescence or cell hyperproliferation in mouse brain (left), kidney (center), liver (right) shown at low (upper) and at 40× magnification (lower).

This document provides methods and materials related to treating cardiovascular tissue (e.g., heart tissue or vascular tissue). For example, this document provides stem cells, compositions containing stem cells, methods for obtaining stem cells, compositions for generating stem cells expressing particular markers, and methods for repairing cardiovascular tissue.

The term "stem cell" as used herein refers to cells that are unspecialized, can renew themselves, and can develop into more mature, specialized cells. In some cases, a stem cell can be unspecialized while being committed to differentiate into a particular type of specialized cell to the exclusion of other types of specialized cells. For example, a stem cell can be committed to develop into cardiomyocytes and not neurons. Stem cells can be obtained from various tissues. For example, stem cells such as embryonic stem cells can be obtained from embryos, embryoid bodies, or fetal tissue, while stem cells such as adult stem cells can be obtained from adult tissue.

The stem cells provided herein can have the ability to differentiate into cardiomyocytes. Such stem cells can be used to replace diseased or damaged heart tissue (e.g., myocardium). In some cases, the stem cells provided herein can result in the production of cardiomyocytes without producing tumor cells for a period of time following, for example, implantation. Such a time period can be one, two, three, four, five, six, seven, eight, nine, ten, or more months. In some cases, the time period can be one, two, three, four, five, six, or more years. For example, the stem cells provided herein can result in the production of cardiomyocytes without producing tumor cells for at least one, two, three, or more years following implantation within a human.

The stem cells provided herein can express any combination of polypeptides. For example, the stem cells provided herein can express one or more polypeptides (e.g., one, two, three, four, or five polypeptides) that are also expressed by embryonic stem cells but not cardiomyocytes. Such polypeptides include, without limitation, Oct4; DEK; BRCA1; Ect2; and MYC polypeptides. The stem cells provided herein can contain all of these polypeptides or any combination thereof (e.g., Oct4, BRCA1, Ect2, and MYC polypeptides; or Oct4, DEK, BRCA1, and MYC polypeptides; or Oct4, DEK, BRCA1, and Ect2 polypeptides).

In some cases, the stem cells provided herein can express one or more polypeptides (e.g., one, two, three, four, five, six, seven, eight, nine, ten, or more polypeptides) that are also expressed by cardiomyocytes but not embryonic stem cells. Such polypeptides include, without limitation, Fosb; NRAP; MEF2A; Furin; TGFβ1; fibronectin receptor α; discoidin domain receptor 1; bag2; cystein rich protein; CUGBP2; NDRG4; CBP/p300 inhibitory protein 1; interferon inducible protein 1; tropomyosin 1, alpha; Rho GTPase activating protein 1; carboxypeptidase D; profilin 2; transforming growth factor beta 1 induced transcript 1; tropomyosin 1, alpha; growth hormone receptor; vinculin; adenylate cyclase 6; S100 calcium binding protein A1; tropomyosin 2, beta; retinol binding protein 1, cellular; Moesin; matrix metalloproteinase 2; secreted acidic cysteine rich glycoprotein; mannosidase 1, alpha; lectin, galactose binding, soluble 1; S100 calcium binding protein A6 (calcyclin); epoxide hydrolase 1, microsomal; pleiomorphic adenoma gene-like 1; insulin-like growth factor 2; tubby like protein 4; prion protein; FK506 binding protein 10; cyclin D2; reticulocalbin 3, EF-hand calcium binding domain; selenoprotein M; cyclin-dependent kinase inhibitor 1A (P21); caldesmon 1; integrin beta 1 (fibronectin receptor beta); transcobalamin 2; annexin A2; cyclin-dependent kinase inhibitor 1A (P21); thrombospondin 1; monocyte to macrophage differentiation-associated; AXL receptor tyrosine kinase; annexin A5; muscleblind-like 2; annexin A1; procollagen, type IV, alpha 1; calpain 2; epithelial membrane protein 1; protease, serine, 11; tropomyosin 2, beta; lectin, galactose binding, soluble 9; and annexin A3 polypeptides. The stem cells provided herein can contain all of these polypeptides or any combination thereof (e.g., vinculin, annexin A5, CUGBP2, NDRG4, and profilin 2 polypeptides; or NRAP, MEF2A, Furin, TGFβ1, and fibronectin receptor a polypeptides; or Fosb, Rho GTPase activating protein 1, FK506 binding protein 10, annexin A3, and NDRG4 polypeptides).

In some cases, the stem cells provided herein can express one or more polypeptides (e.g., one, two, three, four, five, six, seven, eight, or more polypeptides) that are not expressed by cardiomyocytes nor embryonic stem cells. Such polypeptides include, without limitation, integral membrane protein 2A; insulin-like growth factor binding protein 4; thymus cell antigen 1, theta; selenoprotein P, plasma, 1; glycoprotein 38; epidermal growth factor receptor pathway substrate 8; heat shock protein 1A; cellular retinoic acid binding protein I; and placenta-specific 8 polypeptides. The stem cells provided herein can contain all of these polypeptides or any combination thereof (e.g., insulin-like growth factor binding protein 4, heat shock protein 1A, and integral membrane protein 2A polypeptides; or integral membrane protein 2A, cellular retinoic acid binding protein I, and placenta-specific 8 polypeptides; or glycoprotein 38, epidermal growth factor receptor pathway substrate 8, cellular retinoic acid binding protein I, and placenta-specific 8 polypeptides).

The stem cells provided herein can express any number of different polypeptides and can express polypeptides at any level as compared to the levels observed in other cells. For example, a stem cell having the ability to differentiate into cardiomyocytes can express Oct4, DEK, BRCA1, Ect2, and MYC polypeptides at a level less than the levels observed in embryonic stem cells. In some cases, a stem cell having the ability to differentiate into cardiomyocytes can express matrix metalloproteinase 2; secreted acidic cysteine rich glycoprotein; mannosidase 1, alpha; lectin, galactose binding, soluble 1; S100 calcium binding protein A6 (calcyclin); epoxide hydrolase 1, microsomal; pleiomorphic adenoma gene-like 1; insulin-like growth factor 2; tubby like protein 4; and prion protein polypeptides at a level less than the levels observed in cardiomyocytes. The level of other polypeptides with respect to the levels observed in other cells (e.g., embryonic stem cells or cardiomyocytes) are provided in Table 1.

Any method can be used to obtain stem cells. For example, stem cells having the ability to produce cardiomyocytes without resulting in the production of tumor cells as well as stem cells expressing one or more of the polypeptides listed as present in the third column of Table 1 can be obtained by contacting stem cells such as embryonic stem cells with a cardiogenic cocktail. Stem cells such as embryonic stem cells can be contacted with a cardiogenic cocktail for one, two, three, four, five, or more hours (e.g., one, two, three, four, five, or more days) under culture conditions.

A cardiogenic cocktail can be a solution that contains, without limitation, one or more of the following polypeptides: TGF-β1; TGF-β2; BMP-1; BMP-2; BMP-5; BMP-6; FGF-4; FGF-5; FGF-12; FGF-13; FGF-15; FGF-20; leukemia inhibitory factor (LIF); VEGF-C; interleukin 6; caspase-4; chemokine ligand 1; chemokine ligand 2; chemokine ligand 5; chemokine ligand 7; chemokine ligand 11; chemokine ligand 20; haptoglobin; colony stimulating factor-1; lectin; cholesterol 25-hydroxylase; syntaxin-8; syntaxin-11; ceruloplasmin; complement component 1; complement component 3; platelet derived growth factor; integrin alpha 6; lysosomal acid lipase 1; interleukin 6; β-2 microglobulin; ubiquitin; macrophage migration inhibitory factor; retinoic acid; BMP-4; cofilin; cyclophillin A; FKBP 12; NDPK; profilin 1; cystatin C; and calcyclin. For example, a cardiogenic cocktail can contain TGF-β1; TGF-β2; BMP-1; BMP-2; BMP-5; BMP-6; FGF-4; FGF-5; FGF-12; FGF-13; FGF-15; FGF-20; leukemia inhibitory factor (LIF); VEGF-C; and interleukin 6.

Any method can be used to make a cardiogenic cocktail. For example, culture media can be supplemented with commercially-available polypeptide preparations such as commercially-available TGF-β1 or IL-6 polypeptides. In some cases, a cardiogenic cocktail can be obtained by culturing ventral endodermal cells or ventral endodermal-like cells and collecting the resulting conditioned medium, which can contain a cocktail of polypeptides that has the ability to cause, for example, embryonic stem cells to lose their tumorigenicity and to commit to differentiating into cardiomyocytes. Ventral endodermal cells can be obtained from an embryo such as a mouse, rat, human, bovine, or porcine embryo. The endoderm can be cardiotrophically primed by treatment of the embryo with a cardiotrophic-enhancing agent (e.g., a TNF-α polypeptide) to induce an increased expression of cardiogenic cocktail components. Representative ventral endodermal-like cells include, without limitation, embryonal carcinoma cells. In some cases, exogenous IGF-1, IL-6, FGF-4, TGF-β, BMP, LIF, and hα-thrombin polypeptides (or any combination thereof) can be added to the conditioned medium. For example, conditioned medium to which about 50 ng/mL IGF-1, about 100 ng/mL IL-6, about 10 ng/mL FGF-4, about 25 ng/mL TGFβ, about 5 ng/mL BMP, about 100 U/mL LIF, and about 40 nM hα-thrombin has been added can be used as a cardiogenic cocktail to drive cardiogenesis of stem cells (e.g., embryonic stem cells).

After contacting stem cells (e.g., embryonic stem cells) with a cardiogenic cocktail, the stem cells can differentiate into stem cells having the ability to produce cardiomyocytes and not another cell type (e.g., a tumor cell). Such cells can be referred to as cardiopoietic stem cells. Cardiopoietic stem cells can exhibit nuclear translocation of cardiac transcription factors (e.g., Nkx2.5, MEF2C, and GATA4), demonstrative of definitive commitment to the cardiac fate. Cardiopoietic stem cells also can lack cellular plasticity, which can be demonstrated, in part, by down-regulated expression of markers of both pluripotency and oncogenesis. Cardiopoietic stem cells can exhibit contact inhibition in culture, a phenomenon not observed with pluripotent embryonic stem cells. Cardiopoietic stem cells can represent a transitional state during cardiogenic metamorphosis from a phenotype of high nucleus to cytosol ratio, typical of embryonic stem cells, towards acquisition of a striated cardiomyocyte structure. Distinct from their pluripotent source or cardiomyocyte progeny, cardiopoietic stem cells can exhibit features of definitive commitment to the cardiac program including upregulation of cardiac transcription factors in the absence of excitation-contraction components. Cardiopoietic stem cells can be highly proliferative, likely because they are not impeded by the mitotic burden of sarcomeric organization.

Any method can be used to obtain a stem cell that expresses a particular combination of polypeptides. For example, a cardiopoietic stem cell can be obtained by culturing embryonic stem cells with a cardiogenic cocktail. Once obtained, the cardiopoietic stem cell can be treated with antisense oligonucleotides, rybozymes, RNA interference constructs, or a combination thereof to reduce the expression of one or more particular polypeptides. In some cases, standard gene knock-out technology can be used to make cells, embryos, or mammals lacking expression of one or more particular polypeptides. Such cells, embryos, and mammals then can be used as a source for embryonic stem cells that can be treated with a cardiogenic cocktail to obtain, for example, cardiopoietic stem cells lacking expression of one or more particular polypeptides.

Any method can be used to determine whether or not a sample (e.g., biological sample such as an embryoid body) contains a stem cell having one or more of the characteristics described herein. For example, cells can be examined using RT-PCR or immunocytochemistry to determine whether or not the cells express one or more of the polypeptides listed in the third column of Table 1. In vitro or in vivo experiments similar to those described herein can be used to identify stem cells capable of differentiating into cardiomyocytes without producing tumor cells.

The stem cells provided herein can be used to make a composition containing stem cells. Such a composition can contain an enriched population of the stem cells provided herein. For example, a composition can contain cells such that at least 3, 5, 10, 20, 25, 30, 35, 40, 50, 60, 70, 80, 90, 95, 99, or 100 percent of the cells of the composition are the stem cells provided herein. Any method can be used to make an enriched population of stem cells. For example, culturing techniques can be used to expand a stem cell population as opposed to other cells within the culture. In some cases, separation techniques (e.g., Percoll gradients) can be used to separate cardiopoietic stem cells from other cells such as embryonic stem cells and cardiomyocytes. A composition containing an enriched population of the stem cells provided herein can contain additional components such as a cardiogenic cocktail or culture media designed to maintain the differentiation state of the stem cells.

The stem cells provided herein can be used to treat cardiovascular tissue. For example, the stem cells provided herein can be administered to injured cardiovascular tissue (e.g., cardiac tissue) within a mammal such as a human, monkey, horse, sheep, cow, pig, dog, cat, or rodent. Such injured tissue can be tissue damaged by ischemia and/or infarction. In some cases, the injured tissue can be tissue damaged congenitally. In these cases, the stem cells provided herein can be administered immediately after birth or prenatally.

While not being limited to any particular mode of action, the administered stem cells can differentiate into cardiomyocytes that incorporate into injured cardiac or vascular tissue, thereby repairing the injury. In some embodiments, the stem cells can express the polypeptides listed in the third column of Table 1. Any method can be used to administer the stem cells to cardiovascular tissue. For example, a catheter can be used to deliver the stem cells to an injured region of cardiac or vascular tissue. In some cases, the stem cells can be directly injected into the injured tissue or can be placed directly onto or into the heart if the recipient is, for example, already undergoing an open chest procedure.

This document also provides methods for treating cardiovascular tissue with embryonic stem cells under conditions wherein tumors do not develop for a period of time after implantation. Such a time period can be one, two, three, four, five, six, seven, eight, nine, ten, or more months. In some cases, the time period can be one, two, three, four, five, six, or more years. Typically, embryonic stem cells can be administered to a recipient using a relatively small number of embryonic stem cells so that the administered embryonic stem cells result in the production of cells (e.g., cardiomyocytes) without producing tumor cells. For example, embryonic stem cells can be administered in an amount less than about 1500 embryonic stem cells per mg of cardiovascular tissue (e.g., less than about 1400, 1200, 1000, 800, 500, or 300 embryonic stem cells per mg of cardiovascular tissue).

Any of the methods provided herein for treating cardiovascular tissue can include additional treatments. For example, growth factors or cytokines such as TNFα or γ-interferon, or any combination thereof can be administered to the cardiovascular tissue being treated. The growth factors or cytokines can be administered to cardiovascular tissue before or after stem cells (e.g., the stem cells provided herein, embryonic stem cells, or a combination thereof) are administered. In some cases, the growth factors or cytokines can be administered with the stem cells (e.g., the stem cells provided herein, embryonic stem cells, or a combination thereof). While not being limited to any particular mode of action, growth factors and cytokines such as TNFα or γ-interferon can cause cardiovascular tissue (e.g., heart tissue) to produce polypeptides that create an environment favorable for the differentiation of stem cells into cardiomyocytes without producing tumor cells.

The invention will be further described in the following examples, which do not limit the scope of the invention described in the claims.

EXAMPLES

Example 1

Materials and Methods for Embryonic Stem Cell Therapy in Myocardial Infarction

Embryonic Stem Cells.

The CGR8 murine embryonic stem cell line was propagated in BHK21 or Glasgow MEM medium supplemented with pyruvate, non-essential amino acids, mercaptoethanol, 7.5% fetal calf serum, and the leukemia inhibitory factor (Meyer et al., 2000, *FEBS Lett.*, 478:151-158; Perez-Terzic et al., 2003, *Circ. Res.*, 92:444-452). A CGR8 cell clone was engineered to express the yellow fluorescent protein (YFP) or the enhanced cyan fluorescent protein (ECFP) under the control of the cardiac-specific α-actin promoter subcloned upstream of ECFP using XhoI and HindIII restriction sites of the promoterless pECFP vector (Clontech). This α-actin promoter construct was linearized using XhoI, and electroporated into CGR8 stem cells as described (Behfar et al., 2002, *FASEB J.*, 16:1558-1566; Meyer et al., 2000, *FEBS Lett.*, 478:151-158). To image stem cells by field-emission scanning electron microscopy, cells were fixed in phosphate-buffered saline containing 1% glutaraldehyde and 4% formaldehyde (pH 7.2), dehydrated with ethanol and dried in a critical point dryer. Cells, coated with platinum using an Ion Tech indirect argon ion-beam sputtering system (VCR Group), operating at accelerating voltages of 9.5 kV and 4.2 mA, were then examined on a Hitachi 4700 field-emission scanning microscope (Perez-Terzic et al., 2001, *J. Biol. Chem.*, 276: 20566-20571). For transmitted scanning electron microscopy, stem cells were post-fixed in phosphate-buffered 1% $OsO_4$, stained en bloc with 2% uranyl acetate, dehydrated in ethanol and propylene oxide, and embedded in low viscosity epoxy resin. Thin (90-nm) sections were stained with lead citrate, and micrographs taken on a JEOL 1200 EXII electron microscope (Hodgson et al., 2003, *EMBO J.*, 22:1732-1742).

Stem Cell-Derived Cardiomyocytes.

CGR8 embryonic stem cells were differentiated in vitro using the previously established hanging-drop method to generate embryoid bodies (Behfar et al., 2002, *FASEB J.*, 16:1558-1566; Maltsev et al., 1994, *Circ. Res.*, 75:233-244). Following enzyme dissociation of embryoid bodies, Percoll gradient was used to isolate a highly enriched population of stem cell-derived cardiomyocytes as described (Perez-Terzic et al., 2003, *Circ. Res.*, 92:444-452). The presence of cardiac markers in purified cells was probed by laser confocal microscopy (Zeiss LSM 510 Axiovert) using anti-MEF2C (Cell Signaling Technology) and anti-α actinin (Sigma) antibodies. Membrane electrical activity was determined by patch clamp recording in the whole cell configuration using the current- or voltage-clamp mode (Axopatch 1C, Axon Instruments). Action potential profiles and voltage/current relationship were acquired and analyzed with the Bioquest software from cells superfused with Tyrode solution (in mM: NaCl 137, KCl 5.4, $CaCl_2$ 2, $MgCl_2$ 1, HEPES10, glucose 10; pH 7.4 with NaOH) using patch pipettes (5-10 MW) containing (in mM) KCl 140, $MgCl_2$ 1, HEPES10, EGTA 5, and supplemented with 5 mM ATP (pH 7.2 adjusted with KOH). Electrophysiological measurements were performed at 31±1° C. using a temperature controller (HCC-100A, Dagan Corp.) equipped with a Peltier thermocouple (Zingman et al., 2002, *J. Biol. Chem.*, 277:14206-14210). To assess intracellular $Ca^{2+}$ dynamics, cells were loaded with the $Ca^{2+}$-fluorescent probe Fluo3-AM (Molecular Probes), line-scanned with a Zeiss laser confocal microscopy, and analyzed using an imaging software (Zeiss LSM Image Browser) as described (Perez-Terzic et al., 2003, *Circ. Res.*, 92:444-452; Zingman et al., 2002, *Proc. Natl. Acad. Sci. USA*, 99:13278-13283).

Myocardial Infarction Model.

Myocardial infarction was induced at 6-weeks of age by ligation of the left anterior descending coronary artery in male Sprague Dawley rats resulting in an established model with an approximately 30% infarcted left ventricle (Charles River). Consequently, left ventricular ejection fraction was depressed from 75±2% at baseline to 47±3% post-infarct. Infarcted animals were randomized into sham- and embryonic stem cell-treatment groups. Eight weeks after infarct, animals were anesthetized with isoflurane (3% induction, 1.5% maintenance), 12-lead electrocardiography was performed, and the heart exposed by thoracotomy. Medium (20 µL Glasgow MEM) without cells (sham) or CGR8 embryonic stem cells ($3\times10^5$ in 20 µL medium), engineered to express enhanced cyan fluorescent protein (ECFP) under control of the cardiac specific actin promoter, were injected through a 28-gauge needle at three sites (at the left ventricular base just below the left atrium, in the mid anterior region, and at the apex) along the border of the left ventricular infarcted areas.

Electrocardiography.

Twelve-lead electrocardiography was performed under isoflurane anesthesia using subcutaneous needle electrodes (Grass Instruments) and a differential electrocardiographic amplifier (Model RPS312, Grass Instruments). Standard and augmented limb leads (I, II, III, aVR, aVL, aVF) as well as precordial leads (V1-V6) were recorded prior to sham/stem cell injection and serially thereafter.

Echocardiography.

Under isoflurane-anesthesia, two-dimensional M-mode echocardiographic images were obtained from the parasternal short-axis view with a 5 MHz probe at the ventricular base (Vingmed System FiVe, GE Medical Systems). Using the leading-edge convention of the American Society of Echocardiography, ejection fraction (EF) was calculated as EF=100 $(D^2-S^2)/D^2$ where D is the end-diastolic cavity diameter and S is the end-systolic cavity diameter (Behfar et al., 2002, *FASEB J.*, 16:1558-1566; Hodgson et al., 2003, *EMBO J.*, 22:1732-1742).

Histopathology.

On autopsy, gross pathological examination was performed on 4% formalin-fixed transverse-cut hearts, followed by light microscopy of 0.5-nm thick paraffin sections stained with hematoxylin-eosin (Zingman et al., 2002, *Proc. Natl. Acad. Sci. USA*, 99:13278-13283). The fraction of chamber circumference with residual post-infarction left ventricular scar was determined in standardized sections through the left ventricular base at the mid-level of infarct. Fluorescent microscopy (Zeiss) was performed on unstained paraffin sections. For transmitted electron microscopy, myocardial specimens were post-fixed in phosphate-buffered 1% $OsO_4$, stained en bloc with 2% uranyl acetate, dehydrated in ethanol and propylene oxide, and embedded in low viscosity epoxy resin. Thin (90-nm) sections were cut on an ultramicrotome (Reichert Ultracut E), placed on 200-nm mesh copper grids, and stained with lead citrate. Micrographs were taken on a JEOL 1200 EXII electron microscope operating at 60 kV (Hodgson et al., 2003, *EMBO J.*, 22:1732-1742).

Statistics.

Values are expressed as mean±standard error. Embryonic stem cell-treated versus sham-treated groups were compared using the Student's t test with a p value<0.05 considered significant. The Wilcoxon log-rank test was used for nonparametric evaluation of randomization.

Example 2

Embryonic Stem Cell Therapy in Myocardial Infarction

Cardiogenic Potential of Embryonic Stem Cells and Delivery into Infarcted Heart.

Figure 2:
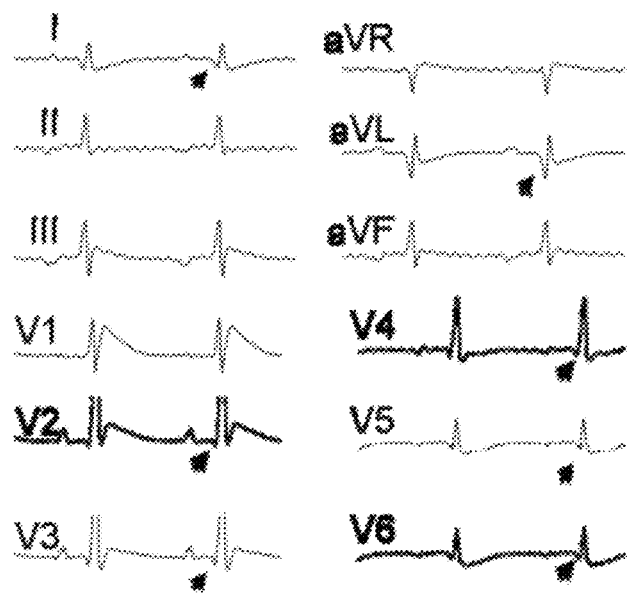
FIG. 2 shows infarction of rat hearts confirmed by the presence of anterior and lateral Q-waves on 12-lead electrocardiogram (FIG. 2A) and by visual inspection following thoracotomy (FIG. 2B).
Figure 2:
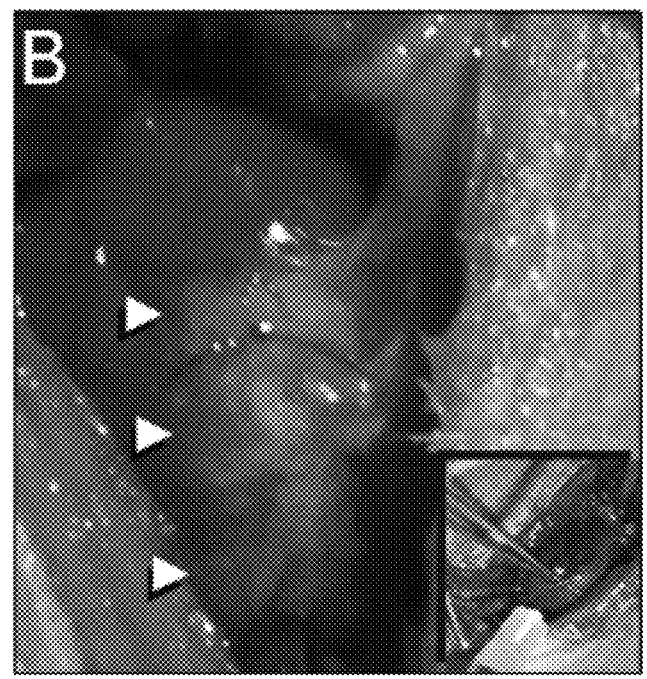

The CGR8 embryonic stem cell colony, used herein (FIG. 1A), demonstrated typical features of undifferentiated cells including a high nucleus to cytosol ratio, prominent nucleoli and mitochondria with few cristae (FIG. 1B). The cardiogenic capacity of this embryonic stem cell line was probed by in vitro differentiation, with cells readily derived that express the cardiac transcription factor MEF2C (Lin et al., 1997, *Science*, 276:1404-1407), the cardiac contractile protein α-actinin and sarcomeric striations (FIG. 1C). Consistent with proper differentiation towards cardiac lineage, stem cell-derived cardiomyocytes demonstrated action potential activity associated with prominent inward $Na^+$ and $Ca^{2+}$ currents (FIG. 1D), critical for excitation-contraction coupling manifested as rhythmic intracellular $Ca^{2+}$ transients (FIG. 1E). Injection of CGR8 cells into myocardium resulted in local retention of these embryonic stem cells (FIG. 1F) without detectable dispersal into non-cardiac tissues (FIG. 1G). To determine the outcome of stem cell therapy for cardiac repair in myocardial infarction, rats were randomly assigned to stem cell or sham treatment groups. Eight weeks following left anterior descending coronary artery ligation, infarction was confirmed by electrocardiographic evidence of myocardial necrosis (FIG. 2A), as well as by direct visual inspection of the myocardium following thoracotomy (FIG. 2B). Embryonic CGR8 stem cells from the pre-tested colony or acellular preparations (sham controls) were then injected into the peri-infarct zone (FIG. 2B), for assessment of functional and structural impact over time.

Sustained Functional Benefit of Stem Cell- Versus Sham-Treated Infarcted Hearts.

Figure 3:
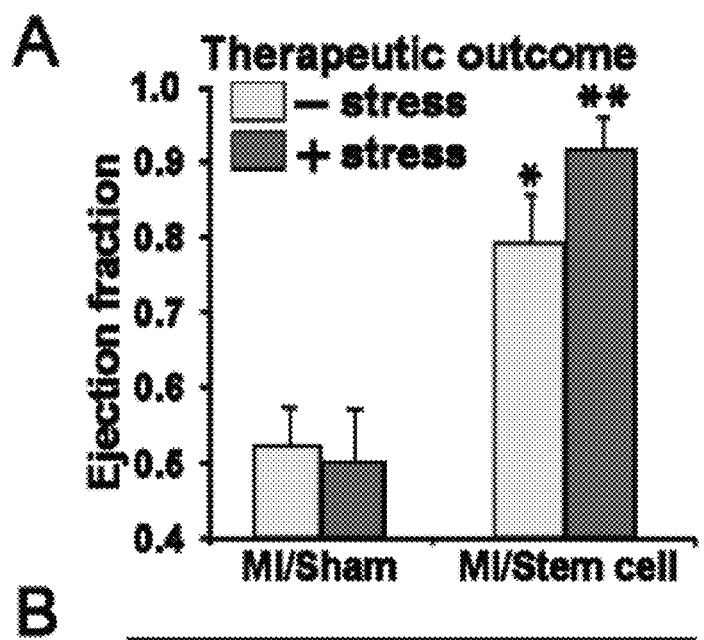
FIG. 3A is a graph showing that at 3 weeks post-injection, left ventricular ejection fraction measured by M-mode echocardiography was significantly greater in stem cell-treated (n=4) versus sham-treated (n=3) infarcted hearts (light grey bars; $p<0.05$). Following stress induced by intraperitoneal injection of isoproterenol, the left ventricular ejection fraction increased in the stem cell-treated group but not in the sham-treated group (dark grey bars; $p<0.05$). A single asterisk represents a significant difference between stem cell and sham groups, while a double asterisk represents a significant difference between stem cell and sham groups as well as a significant difference in the stem cell group with and without stress.
FIG. 3B is a photograph showing a representative M-mode image under stress in the sham-treated heart in contrast to the stem cell-treated heart. Interrupted and continuous lines indicate diastolic and systolic left ventricular dimensions, respectively. MI: myocardial infarction.
Figure 3:
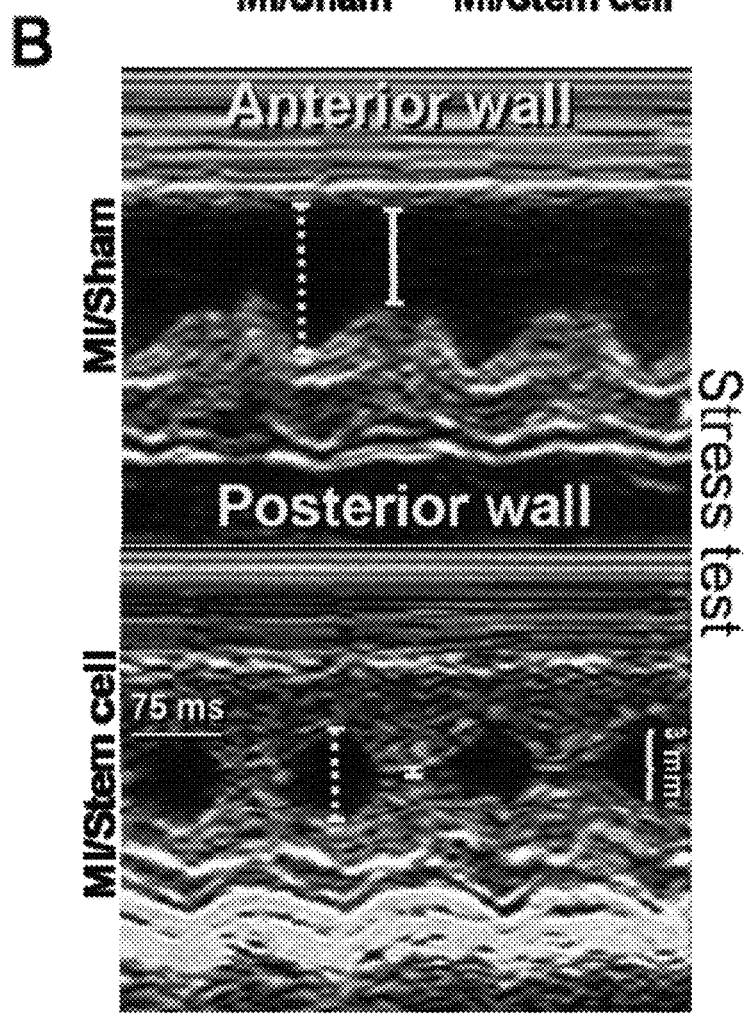
Figure 4:
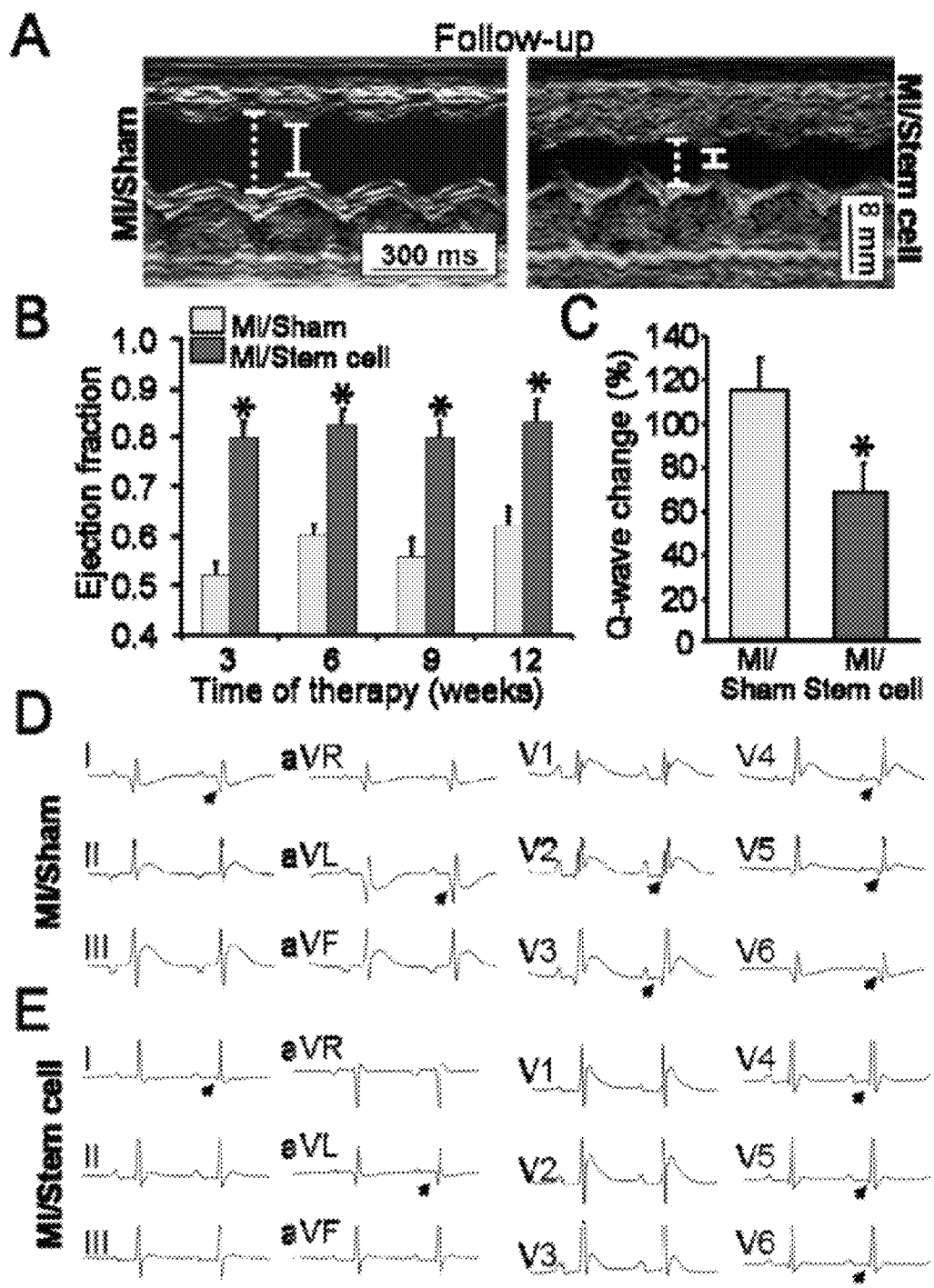
FIG. 4A are representative M-mode images at 12-weeks in sham-treated versus stem cell-treated infarcted hearts. Interrupted and continuous lines indicate diastolic and systolic left ventricular dimensions, respectively.
FIG. 4B shows a graph of serial echocardiographic assessments at 3, 6, 9 and 12 weeks post-therapy.
FIG. 4C shows a graph at 12-weeks compared to initial electrocardiograms in the stem cell-treated and sham-treated group ($p<0.05$).
FIGS. 4D and 4E are representative electrocardiograms from sham-treated (D) and stem cell-treated (E) rats at 12-weeks. Arrowheads indicate location of Q waves. MI: myocardial infarction.

Cardiac contractile function, assessed by echocardiography at 3 weeks post-injection, was superior in embryonic stem cell—compared to sham-treated infarcted hearts (FIG. 3A). On average, left ventricular ejection fraction was 0.80±0.05 versus 0.52±0.05 in the stem-cell versus the sham group, respectively ($p<0.05$). Moreover, while sham-treated infarcted hearts failed to augment function under inotropic challenge, stem cell-treated infarcted hearts demonstrated a significant positive inotropic response. Pharmacologic-stress testing by injection of the β-adrenergic agonist isoproterenol (3 mg/kg), produced a 12% increase in the ejection fraction of stem cell-treated infarcted hearts versus no significant response observed in the sham-treated group (FIG. 3A). M-mode imaging under stress further demonstrated that in contrast to the hypokinetic or akinetic anterior left ventricular walls in sham-treated infarcted hearts, stem cell-injected infarcted hearts exhibit dynamic anterior wall motion with vigorous ventricular function (FIG. 3B). Long-term follow-up found no decay in the contractile advantage of stem cell therapy (FIG. 4). Indeed, the contractile performance benefit of stem cell- versus sham-treated infarcted hearts was maintained at 3, 6, 9 and 12 weeks post-injection, such that at 3 months following cell delivery left ejection fraction was 83±4% and 62±4%, respectively ($p<0.05$; FIGS. 4A and 4B). On M-mode images 3 months post-therapy, the left ventricular dilation and the anterior regional wall motion abnormalities persisted in the sham group but were not seen in the stem cell-treated group (FIG. 4A). Further, electrocardiography performed at 3 months post-therapy revealed in the stem cell-treated group a 33% decrease in the total number of anterior and lateral leads with Q-waves, reflecting net reduction in myocardial necrosis ($P<0.05$), not seen in the sham group (FIG. 4C-4E). Throughout the follow-up period, serial electrocardiograms did not document ventricular ectopy and no animal experienced sudden cardiac death. Thus, delivery of embryonic stem cells into infarcted hearts was associated with a functional benefit at baseline and with stress, and was sustained on follow-up without evidence of proarrhythmia in this model.

Stem Cell Engraftment Associated with De Novo Cardiogenesis and Normalized Myocardial Architecture.

Figure 5:
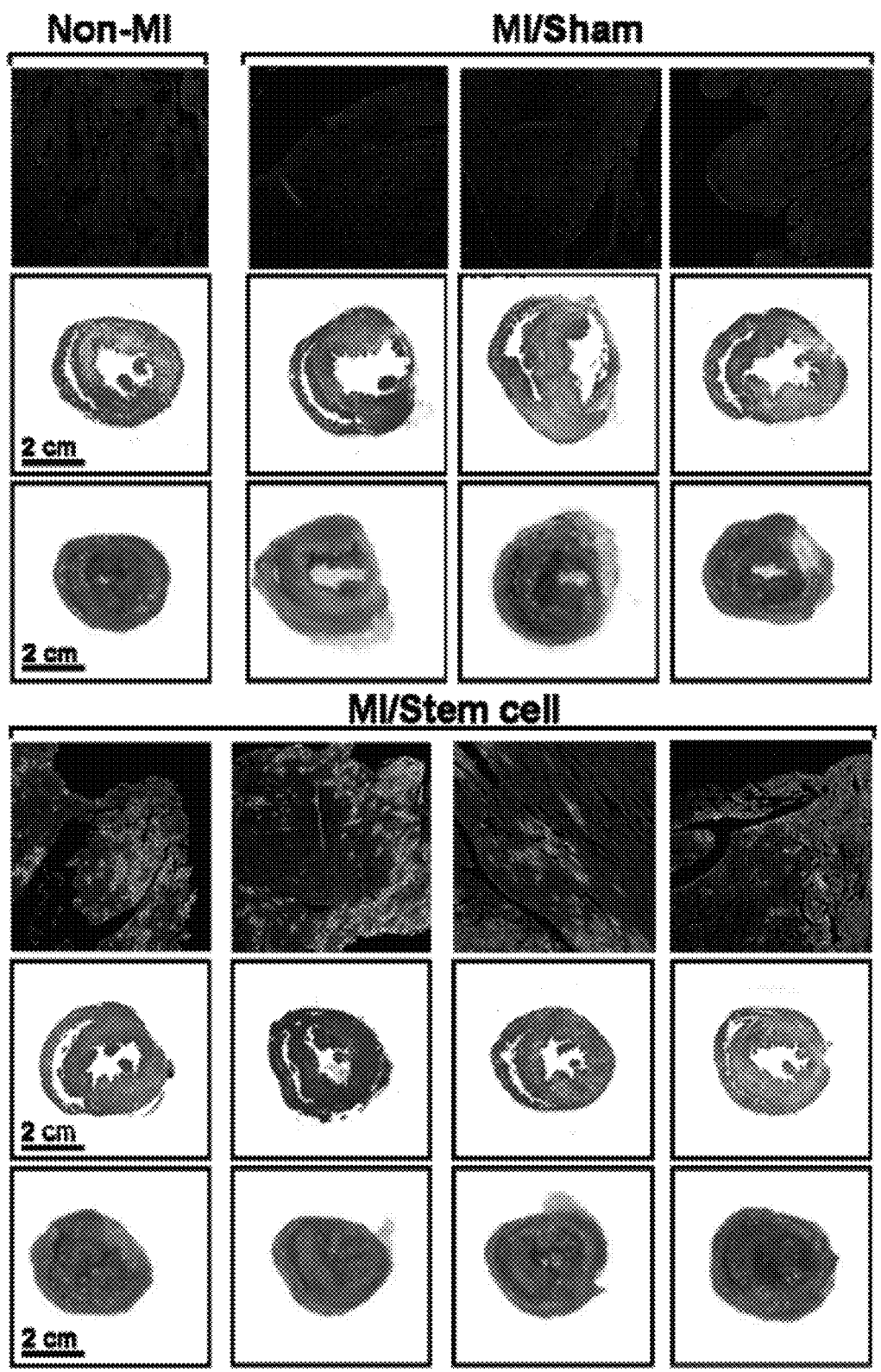
FIG. 5 shows photographs of stem cell-derived cardiomyocytes. The presence of cardiomyocytes derived from injected embryonic stem cells can be demonstrated through expression of the enhanced cyanofluorescent protein under control of the αactin promoter. Fluorescence is not seen in untreated non-infarcted or sham-treated infarcted hearts (Row 1), but is seen within the infarct zone of stem cell-treated hearts (Row 4; 10× magnification). In comparison to non-infarcted hearts, gross specimens and hematoxylin-eosin stained cross sections at the base of each heart within the sham-treated group demonstrate dilated left ventricular cavities and prominent anterolateral scar with aneurysms (Rows 2 and 3). In contrast, left ventricular cavity size and wall thickness are largely preserved in the stem cell-treated hearts (Rows 5 and 6). MI: myocardial infarction.
Figure 6:
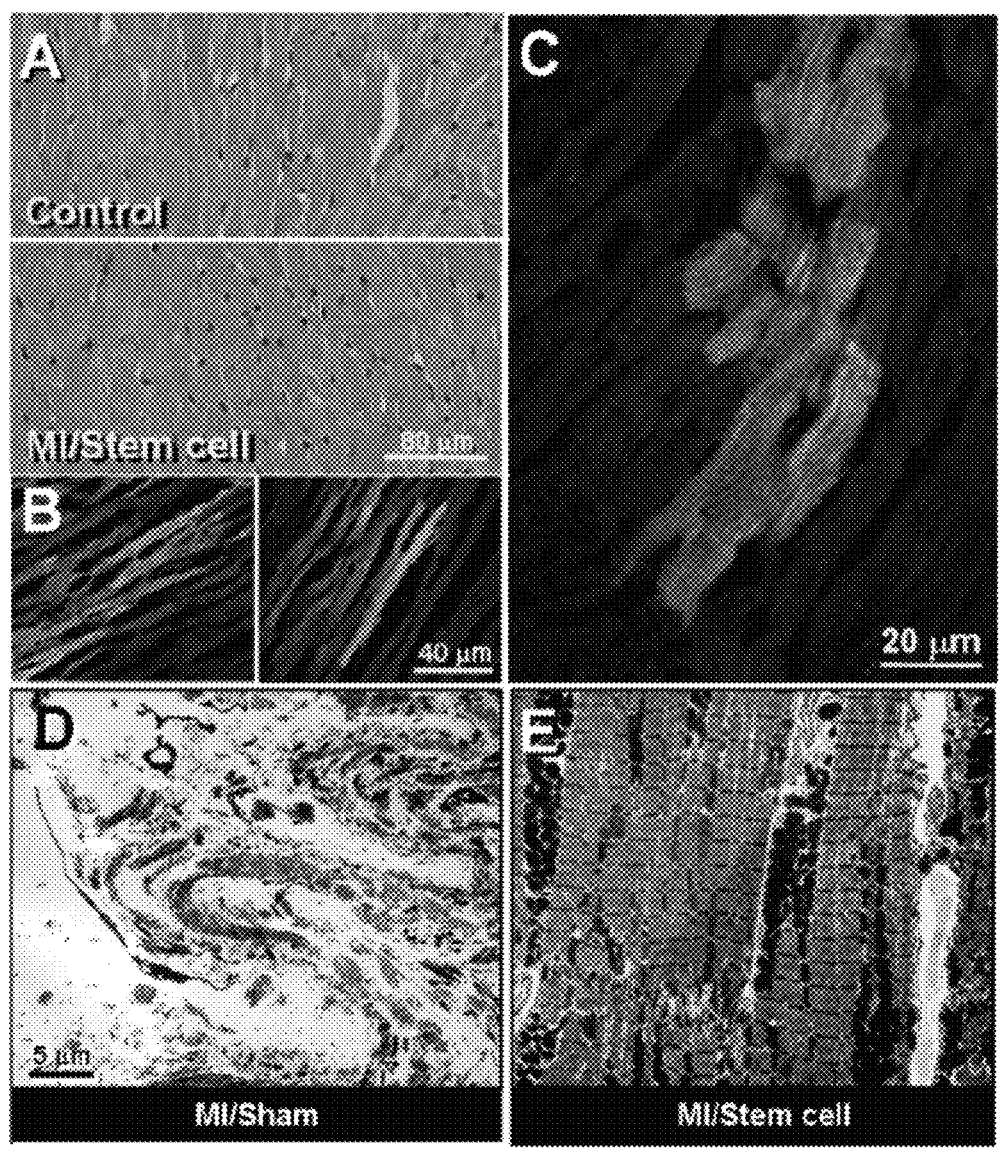
FIG. 6A shows representative hematoxylin-eosin stained myocardial sections in control (upper) or stem cell-injected infarcted hearts (lower).
FIG. 6B-C shows high magnification fluorescence confocal microscopy of stem cell-treated hearts. Stem cell-derived cardiomyocytes organize to form regular fibers (FIG. 6B) oriented along the same axis as host cardiomyocytes (FIG. 6B, 6C), display typical sarcomeric striations and form junctions with non-fluorescent host cardiomyocytes (FIG. 6C).
FIG. 6D-E show representative transmission electron micrographic images of biopsies taken from the infarct zone in sham-treated heart (FIG. 6D) compared to stem cell-treated heart (FIG. 6E).

On pathological examination, the entire group of infarcted hearts treated with stem cells (n=4) demonstrated a population of cyanofluorescent myocytes dispersed within the non-fluorescent host myocardium (FIG. 5, Rows 1 and 4). This fluorescent population, absent from the sham-injected group (n=3), indicates the embryonic stem cell origin through expression of the cyan fluorescent protein under control of the cardiac actin promoter (Behfar et al., 2002, *FASEB J.*, 16:1558-1566). In contrast to sham-treated infarcted hearts that demonstrated markedly altered ventricular architecture with thinned free walls and fibrotic scar or aneurysmal areas comprising 34±11% of the ventricle, the presence of stem cell-derived cardiomyocytes was associated with residual adverse remodeling in only 6±4% of the ventricle ($p<0.05$) and a myocardial appearance more comparable to control non-infarcted heart (FIG. 5, Rows 2-3 and 5-6). Stem cell injected hearts did not demonstrate inflammatory infiltrates that would otherwise suggest an immune response towards the engrafted cells (FIG. 6A). On high magnification, the fluorescent pattern of stem cell-derived cardiomyocytes revealed distinct sarcomeric striations indicating development of the contractile apparatus (FIGS. 6B and 6C). Sarcomeres in the infarct area of stem cell-treated hearts showed normal cardiac ultrastructure on electron microscopy, in contrast to acellular infarct areas of sham-treated hearts (FIGS. 6D and 6E). Thus, embryonic stem cells were able to incorporate within host infarct territory, demonstrate cardiogenic differentiation, and contribute to myocardial repair.

The results provided herein demonstrate a stable favorable impact of embryonic stem cell therapy. This manifested as a sustained benefit on cardiac contractile performance and ventricular remodeling associated with documented cardiogenesis in the infarct zone from injected stem cells. These findings indicate that the advantage of embryonic stem cell delivery occurs early, as first evidenced in the current design at 3-weeks post-therapy, and is not compromised by spontaneous failure of stem cell-derived cardiomyocytes and/or by rejection of this allogenic transplant by the host. The lack of diminishing effect over time suggests the potential for therapeutic use of embryonic stem cells in the chronic management of myocardial injury.

While not being limited to any particular mode of action, several potential mechanisms may account for the demonstrated benefit of embryonic stem cell therapy. Embryonic stem cell-derived cardiomyocytes, through electrical and mechanical coupling with native myocardium, could contribute to a net increase in contractile tissue. Stem cell-derived cardiomyocytes aligned with and integrated within host myocardial fibers. In fact, the host myocardium has been shown to secrete cardiogenic growth factors that interact in a paracrine fashion with receptors on stem cells supporting cardiac differentiation with expression of cardiac contractile and gap junction proteins (Behfar et al., 2002, *FASEB J.*, 16:1558-1566; Mery et al., 2003, *J. Muscle Res. Cell. Motil.*, 24:269-274). The present failure to observe ectopy is further consistent with electrical integration of stem cell-derived cardiomyocytes and host tissue. The stem cell-derived cardiomyocyte effect on active myocardial properties is moreover evidenced here by improved inotropic response to β-adrenergic challenge. A synergistic potential mechanism for functional improvement by stem cell-derived cardiomyocytes is through alteration of myocardial passive mechanical properties (Askari et al., 2003, *Lancet*, 362:697-703), as shown herein by the limited appearance of scar and less dilation of the left ventricle compared to sham treated infarcted hearts. This may occur through direct repopulation of scar by stem cell-derived cardiomyocytes, as well as limitation of adverse remodeling (Britten et al., 2003, *Circulation*, 108:2212-2218; Mangi et al., 2003, *Nat. Med.*, 9:1195-201). Moreover, cell fusion after grafting in vivo has been recently documented with adult stem cells in non-cardiac tissue, as well as with cardiac progenitor cells in the heart itself (Oh et al., 2003, *Proc. Natl. Acad. Sci. USA*, 100:12313-12318; Vassilopoulos et al., 2003, *Nature*, 422:901-904; Wang et al., 2003, *Nature*, 422:897-901). While direct evidence for the propensity of embryonic stem cells to fuse with resident myocardium is lacking, such possibility could in principle further contribute to cardiac repair by lending proliferative capacity to host heart muscle. In this way, cell fusion would complement de novo cardiogenesis occurring with cardiac differentiation of stem cells. As an additional potential mechanism, other cardiovascular cellular types could arise directly from injected stem cells or through in situ recruitment leading to neovascularization and thus augmented metabolic support of the host myocardium (Aicher et al., 2003, *Nat. Med.*, 9:1370-1376; Levenberg et al., 2002, *Proc. Natl. Acad. Sci. USA*, 99:4391-4396; Yang et al., 2002, *J. Appl. Physiol.*, 93:1140-1151). While the mechanism of stem cell-based cardiac repair is thus likely multifactorial, the results provided herein indicate that rather than a transient reorganization that is short-lived due to rejection or failure of the transplant, the initial reparative benefit of stem cell therapy is stable. In fact, no evidence of rejection of the transplanted cells was found despite xenotransplantation of murine embryonic stem cells into rat heart. This lack of host versus graft reaction may be graft- and/or host-dependent due to low expression of immunogenic antigens by stem cells, generation of mixed chimerism, downregulation of host immune response and/or induction of improved tolerance (Drukker et al., 2002, *Proc. Natl. Acad. Sci. USA*, 99:9864-9869; Frandrich et al., 2002, *Nat. Med.*, 8:171-178; Lila et al., 2002, *Circulation*, 105:1949-1954). Finally, disorganized differentiation leading to tumor formation was not observe, although pluripotent stem cells carry this risk (Behfar et al., 2002, *FASEB J.*, 16:1558-1566; Thomson et al., 1998, *Science*, 282:1145-1147) when interacting with the host (Erdo et al., 2003, *J. Cereb. Blood Flow Metab.*, 23:780-785). As previously shown, protection from tumorigenesis is conferred by maintenance of proper host signaling that drives cardiac-specific differentiation of stem cells thus preventing uncontrolled growth (Behfar et al., 2002, *FASEB J.*, 16:1558-1566; Mery et al., 2003, *J. Muscle Res. Cell. Motil.*, 24:269-274).

Thus, the stable benefit of embryonic stem cell therapy on myocardial structure and function in this experimental model supports the potential for stem cell-based reparative treatment of myocardial infarction. By regenerating diseased myocardium and promoting cardiac repair, embryonic stem cells provide a unique therapeutic modality that has the potential to reduce the morbidity and mortality of this prevalent heart disease.

Example 3

Materials and Methods for Allogenic Stem Cells Dosed to Secure Cardiogenesis

Embryonic Stem Cells and Derived Cardiomyocytes.

Field-emission scanning electron microscopy was used to visualize murine embryonic stem cells in culture (Perez-Terzic et al., 2003, *Circ. Res.*, 92:444-452; Hodgson et al., 2004, *Am. J. Physiol.*, 287:H471-H479). Differentiation in vitro was achieved using the hanging-drop method to generate embryoid bodies from which, following enzymatic dissociation, a highly enriched population of cardiomyocytes was isolated with a density gradient protocol (Behfar et al., 2002, *FASEB J.*, 16:1558-1566; Perez-Terzic et al., 2003, *Circ. Res.*, 92:444-452). Expression of cardiac markers was probed by laser confocal microscopy, with action potential activity captured by the patch-clamp method in the current clamp mode (Hodgson et al., 2004, *Am. J. Physiol.*, 287:H471-H479).

Stem Cell Transplantation into Host Heart.

To track transplanted cells in vivo, embryonic stem cells were engineered to express the enhanced cyan fluorescent protein (ECFP) under control of the cardiac-specific α-actin promoter (Behfar et al., 2002, *FASEB J.*, 16:1558-1566; Meyer et al., 2000, *FEBS Lett.*, 478:151-158). Using a 28-gauge needle, engineered stem cells were delivered directly into healthy or infarcted left ventricular walls of isoflurane-anesthetized mice or rats, respectively (Hodgson et al., 2004, *Am. J. Physiol.*, 287:H471-H479). Functional outcome was monitored by short axis 2D and M-mode echocardiography or by ventricular pressure recordings using a micropressure catheter (Behfar et al., 2002, *FASEB J.*, 16:1558-1566; Hodgson et al., 2004, *Am. J. Physiol.*, 287: H471-H479; O'Cochlain et al., 2004, *Hum. Mol. Genet.*, 13:2505-2518). Four to sixteen weeks post-injection, hearts were excised and examined by light and epifluorescent widefield microscopy for structural assessment and presence of stem cell-derived cardiomyocytes, as well as for myocardial electrical activity using the 12-lead electrocardiographic technique (Hodgson et al., 2004, *Am. J. Physiol.*, 287:H471-H479).

Statistics.

Values are expressed as mean±standard error. Embryonic stem cell-treated versus sham-treated groups were compared using the Student's t-test with a p value<0.05 considered significant. The Wilcoxon log-rank test was used for nonparametric evaluation of randomization.

Example 4

Allogenic Stem Cells Dosed to Secure Cardiogenesis

Figure 7:
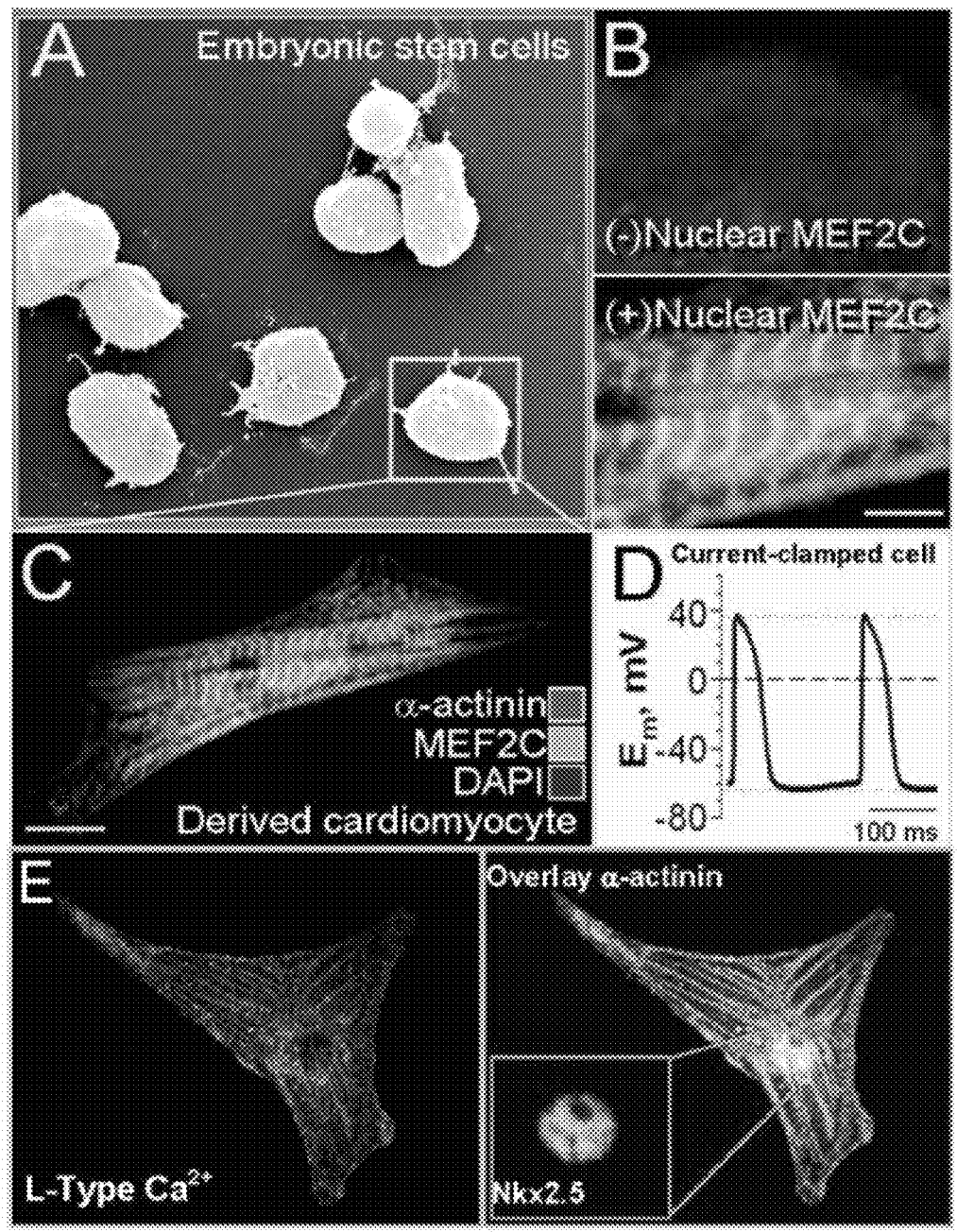
FIG. 7A shows field emission scanning electron microscopy of murine embryonic stem (ES) cells in culture.
FIG. 7B shows laser confocal microscopy of an embryonic stem cell (upper) and derived cardiomyocyte (lower).
FIG. 7C-E shows the cardiac phenotype recapitulated in embryonic stem cell-derived cardiomyocytes including sarcomerogenesis (FIG. 7C), action potential activity (FIG. 7D), L-type calcium channel expression (FIG. 7E), and sustained nuclear localization of the cardiac transcription factor Nkx2.5 (inset). Bars correspond to 5, 4 and 15 μm in A, B and C, respectively. Bar in C applicable also to E.

Cardiogenic potential of embryonic stem cells in vitro. Once established in culture, embryonic stem cells have the capacity to differentiate from a pluripotent to a cardiac phenotype (FIG. 7A-B). This is demonstrated herein as derived cells recapitulated typical cardiomyocyte features including nuclear translocation of cardiac transcription factors, the Myocyte Enhancer Factor 2C (MEF2C) and the homeodomain transcription factor (Nkx2.5) leading to sarcomerogenesis (FIG. 7B-C) and action potential formation associated with L-type $Ca^{2+}$ channel expression (FIG. 7C-E). Thus, embryonic stem cells serve as a reliable cell-based source for de novo cardiogenesis.

Titrated Stem Cell Delivery Secures Cardiogenesis In Vivo.

Figure 8:
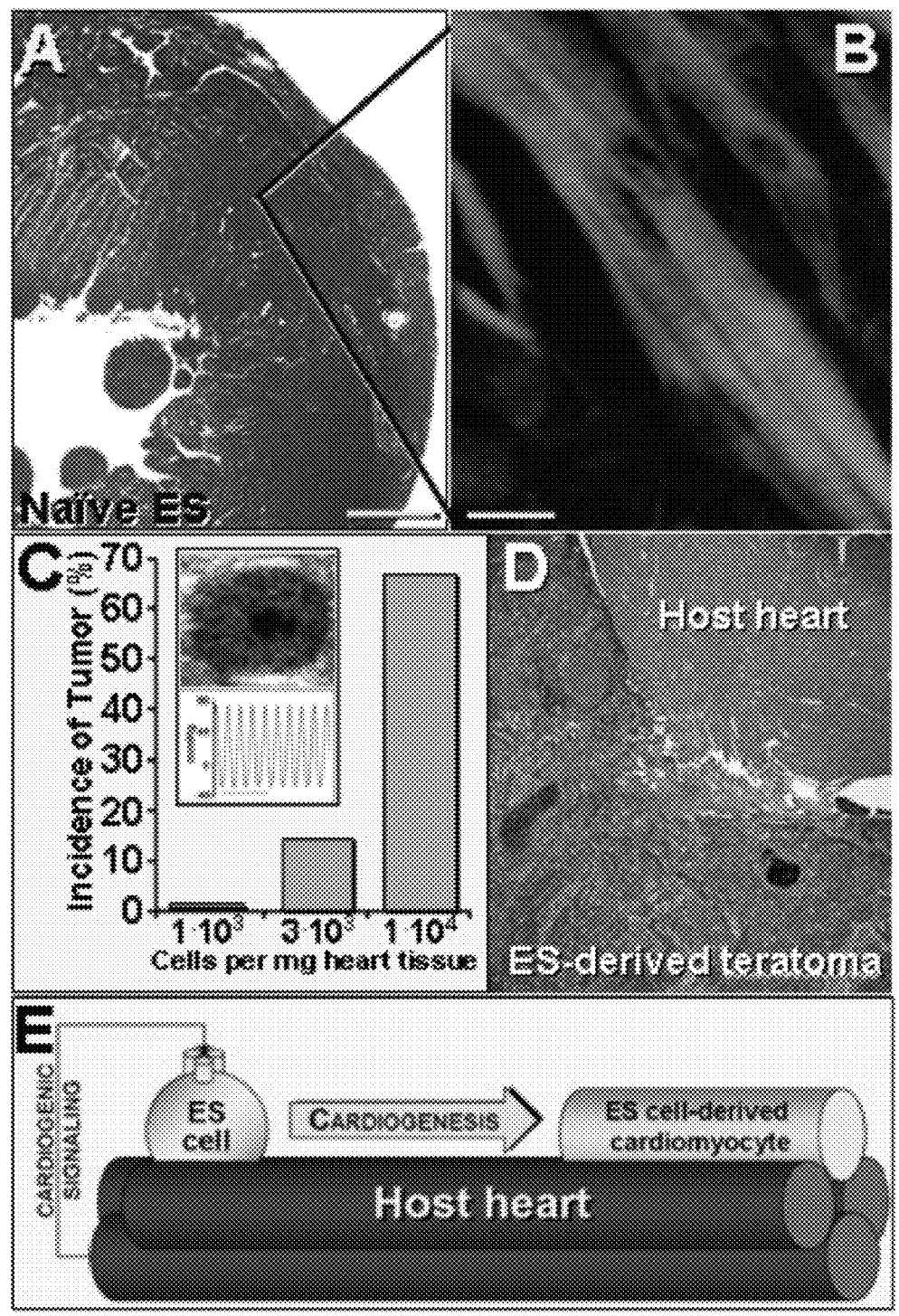
FIG. 8A-B shows that delivery of $10^3$ naïve embryonic stem (ES) cells/mg of host heart tissue results in proper implantation and differentiation with generation of new cardiomyocytes. Bars correspond to 2 mm and 12 μm in A and B, respectively.
FIG. 8C shows that excessive embryonic stem cell load harbors an increase for tumorigenesis. Therapeutic load was established at $10^3$ embryonic stem cells/mg of host heart tissue, which results in safe implantation with no tumor formation, and sustained normal cardiac structure and function (inset).
FIG. 8D shows a photograph of a teratoma generated following delivery of an embryonic stem cell overload ($>10^3$/mg host heart tissue).
FIG. 8E shows a schematic of how a host heart can guide embryonic stem cell differentiation.

Delivery of embryonic stem cells, engineered for in vivo fluorescence tracking, resulted in incorporation into host heart of new cyan fluorescing cardiac cells within the area of stem cell transplantation (FIG. 8A-B). Engraftment of stem cell-derived cardiomyocytes was associated with normal heart morphology (FIG. 8A) and function (FIG. 8C, inset). A threshold in the capacity of the host heart to accept stem cell implantation was established, above which excessive stem cell load compromised cardiogenesis post-transplantation due to uncontrolled differentiation resulting in tumorigenesis (FIG. 8C-D). Thus, the host heart has a finite capacity for driving cardiogenesis in support of differentiation and engraftment of stem cells in vivo (FIG. 8E).

Infarct Repair with Stem Cell Transplantation Yields Stable Outcome.

Figure 9:
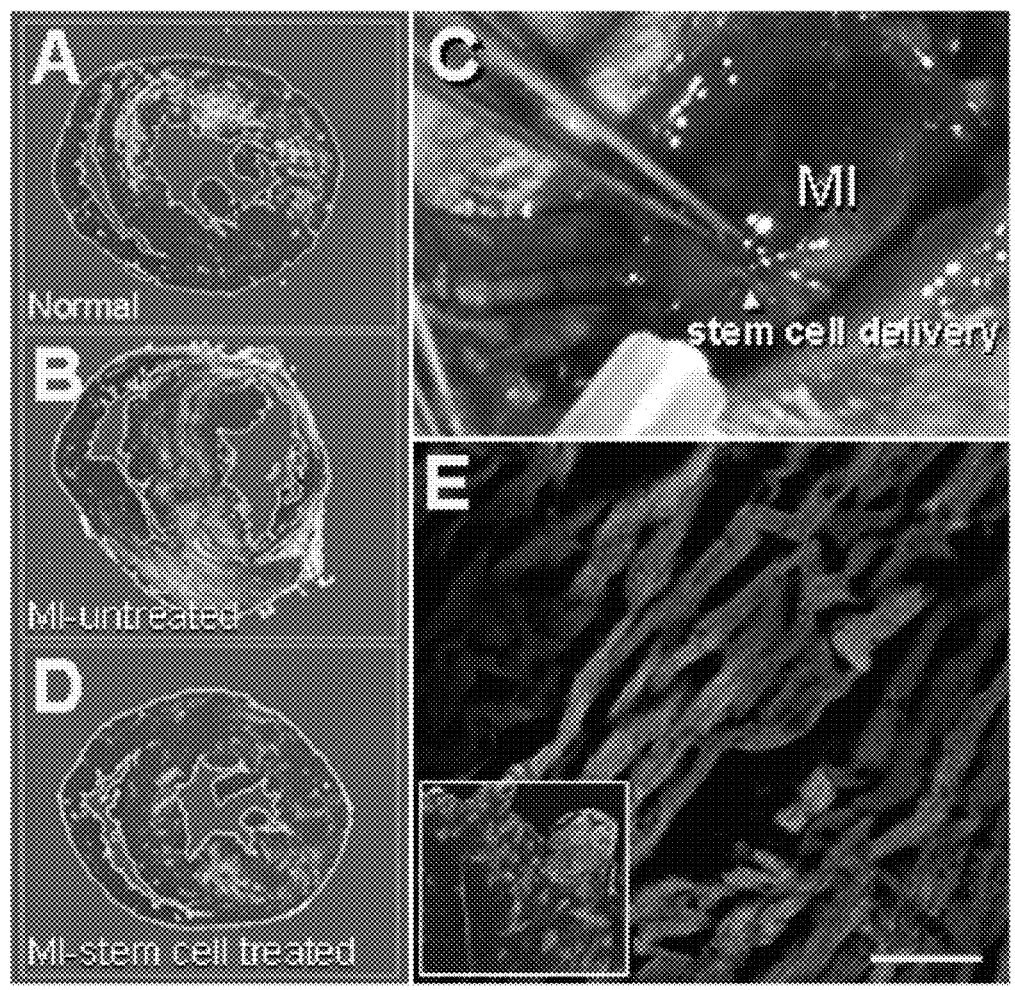
FIG. 9A-D show a comparison of normal (FIG. 9A) versus infarcted hearts either untreated (FIG. 9B) or treated following direct myocardial delivery (FIG. 9C) of stem cells (FIG. 9D).
FIG. 9E shows the presence of stem cell-derived cardiomyocytes. Inset depicts large area of de novo cardiogenesis through low magnification confocal microscopy.
Figure 10:
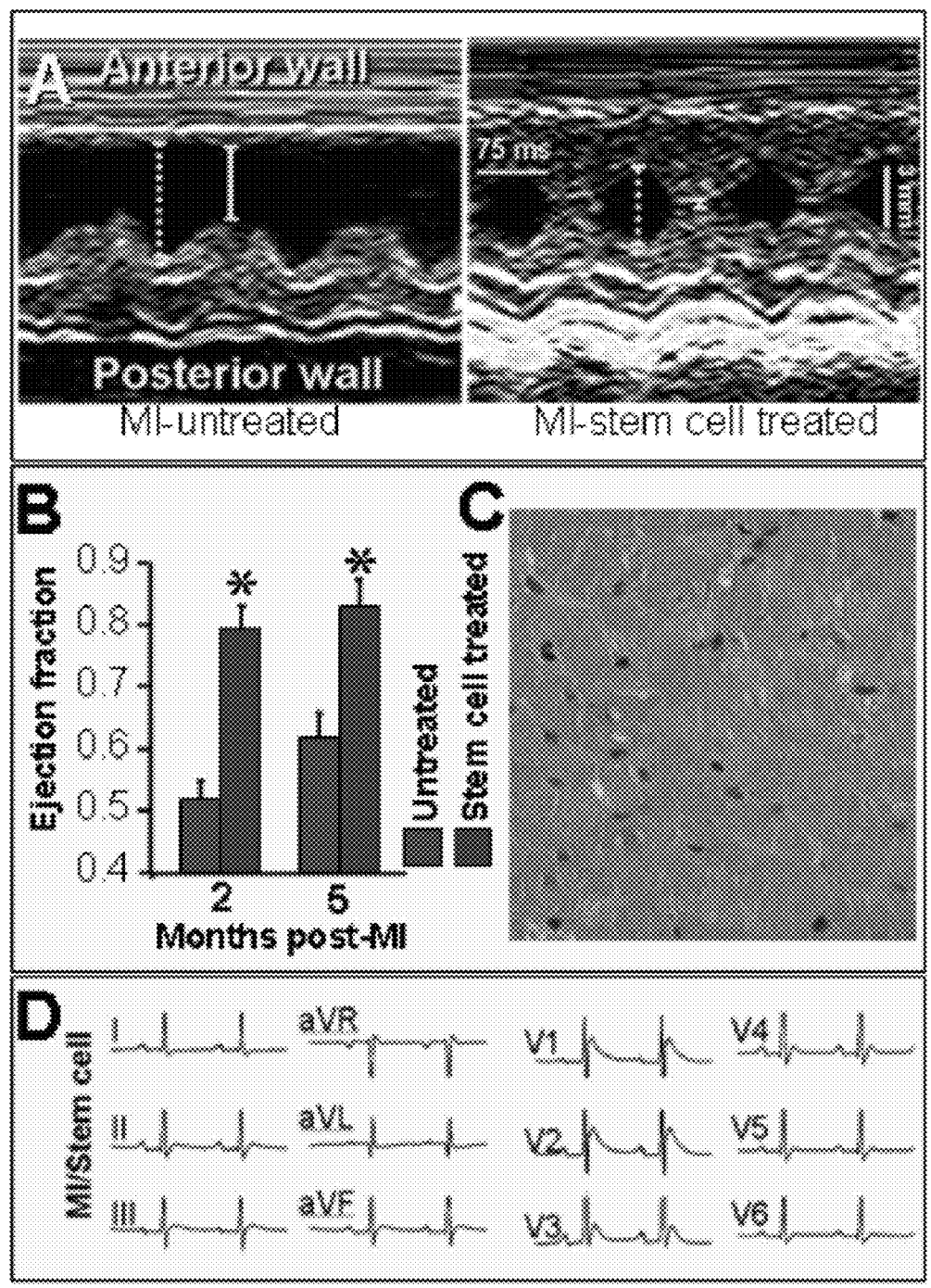
FIG. 10A-B shows an echocardiographic M-mode follow-up demonstrates that stem cell treatment results in normal anterior wall motion and contractile function sustained throughout the 5 month long observation period, without evidence for rejection (FIG. 10C) or arrhythmia (FIG. 10D). Dashed and solid lines indicate diastolic and systolic left ventricular dimensions, respectively.

A myocardial infarct model was generated by coronary ligation, resulting in an aneurysmal and scarred anterior wall with significant compromise in contractile performance (FIG. 9A-B). To test the efficacy of embryonic stem cell-based regeneration of diseased myocardium, embryonic stem cells engineered to fluoresce upon cardiogenesis were delivered by direct myocardial transplantation into peri-infarct area (FIG. 9C). Histopathological examination showed benefit in stem cell-treated infarcted hearts with areas of repair populated by fluorescent cardiac cells indicating stem cell-based de novo cardiogenesis (FIG. 9D-E). In contrast to poorly contracting myocardium in untreated infarcted hearts, stem cell-treated hearts demonstrated synchronous functionally recovered heart muscle on the echocardiographic follow-up (FIG. 10A). Structural repair translated into improvement in the overall ejection fraction in the stem cell-treated group, a benefit maintained over the five month observation period, with no evidence for inflammatory infiltrates (FIG. 10B-C) or arrhythmogenesis (FIG. 10D).

Example 5

Materials and Methods for Procuring Cardioprogenitors

Embryoid Body-Dependent Cardiac Differentiation.

Murine embryonic stem cells were differentiated into embryoid bodies, with cardiogenesis monitored by epifluorescence using α-actinin antibody (1:1,000) and live microscopy (Behfar et al., 2002, FASEB J., 16:1558-1566; Perez-Terzic et al., 2003, Circ. Res., 92:444-452). RNA was processed by real time Q-RT-PCR, using the Light Cycler (Roche) and QuantiTect SYBR Green kit (Qiagen), to quantify Nkx2.5 (forward, reverse primers: 5'-TGC AGA AGG CAG TGG AGC TGG ACA AGC C-3' (SEQ ID NO:1), 5'-TTG CAC TTG TAG CGA CGG TTC TGG AAC CA-3' (SEQ ID NO:2)), MEF2C (5'-AGA TAC CCA CAA CAC ACC ACG CGC C-3' (SEQ ID NO:3), 5'-ATC CTT CAG AGA CTC GCA TGC GCT T-3' (SEQ ID NO:4)), GATA4 (5'-GGA ATT CAA GAT GAA CGG CAT CAA C-3' (SEQ ID NO:5), 5'-TGA ATT CTC AAC CTG CTG GCG TCT TAG A-3' (SEQ ID NO:6)) and βMHC (5'-GCC AAA ACA CCA ACC TGT CCA AGT TC-3' (SEQ ID NO:7), 5'-CTG CTG GAG AGG TTA TTC CTC G-3' (SEQ ID NO:8)) mRNA expression, normalized to β-tubulin (Behfar et al., 2002, FASEB J., 16:1558-1566).

Embryoid Body Free Cardiac Differentiation.

A visceral endoderm-like population (Mummery et al., 2003, Circulation, 107:2733-2740) was derived from F9 cells (ATCC) with retinoic acid (1 µM), dbcAMP (0.5 mM) and theophylline (0.5 mM). Conditioned medium was obtained after 24 h of culture to stimulate cardiogenesis of embryonic stem cells (cultured at 100 cells/cm$^2$) monitored by confocal microscopy.

Cardiopoietic Stem Cell Isolation.

From day 7 embryoid bodies, cardiopoietic stem cells were isolated by Percoll purification and visualized through laser confocal examination using MEF2C (1:400, Cell Signaling Technologies), Nkx2.5 (1:300), GATA4 (1:300, Santa Cruz Biotech), α-actinin (1:1,000, Sigma) and phospho-Smad3 (1:2,000) antibodies. Alternatively, when recruited from a monolayer of embryonic stem cells the cardiopoietic population was enriched using a dual interface Percoll gradient to separate sarcomere-rich high-density cardiomyocytes (Perez-Terzic et al., 2003, Circ. Res., 92:444-452) from the lower-density sarcomere-poor cardiopoietic phenotype. Cardiopoietic stem cell proliferation and purity was assessed by ArrayScan high-throughput multichannel fluorescence automated microscopy (Cellomics) using MEF2C and α-actinin antibodies, along with DAPI staining Action potential profiles and voltage-current relationships were acquired by patch-clamp electrophysiology (Hodgson et al., 2004, Am. J. Physiol., 287:H471-H479). Calcium dynamics were tracked, in Fluo 4-AM loaded cells, using laser confocal line scanning (Perez-Terzic et al., 2003, Circ. Res., 92:444-452; Hodgson et al., 2004, Am. J. Physiol., 287:H471-H479).

Genomics.

Comparative gene expression profiles of embryonic versus cardiopoietic stem cells or cardiomyocytes, as well as unprimed versus TNFα-primed endoderm were attained by labelled cRNA hybridization to the mouse genome 430 2.0 array using standard protocols (Affymetrix). Data was acquired with a GeneChip Scanner 3000 (Affymetrix), and analyzed with the GeneSpring software (Silicon Genetics). Data population sets were normalized to the undifferentiated or unprimed phenotype, and quality filtered to eliminate background noise prior to hierarchical clustering.

Proteomics.

Endodermal cells were cultured with serum-free GMEM. Derived conditioned medium was centrifuged, filtered, quantified (Bradford assay), concentrated (Amicon Ultra 5 kDa cut-off), and re-quantified for volumetric normalization. The protein equivalent of 5 ml conditioned medium was resuspended in isoelectric focusing (IEF) buffer containing urea (7 M), thiourea (2 M), CHAPS (2% w/v) and DeStreak (15 mg/ml, Amersham). Proteins were resolved in the first dimension using immobilized pH gradient IEF strips (BioRad) at pH 3-10, 4-7 and 6-11, and in the second dimension by 7.5% and 15% SDS-PAGE. Proteins, visualized by silver staining, were isolated, destained and trypsin digested (Arrell et al., 2001, Circ. Res., 89:480-487) with extracted peptides subjected to high performance liquid chromatography-electrospray ionization tandem mass spectrometry (ThermoFinnigan LTQ). Proteins were identified using SEQUEST and Mascot search algorithms for in silico mining of the SwissProt database. Identified proteins were further quantified with enzyme-linked immunosorbent assay.

Stem Cell Transplantation.

Under isoflurane anaesthesia, mouse echocardiography with a 15-MHz probe (Acuson) was used to guide myocardial delivery of embryonic or cardiopoietic stem cells engineered for in situ tracking (Behfar et al., 2002, FASEB J., 16:1558-1566). Cardiac performance was monitored by ultrasound imaging in the parasternal short axis with 2-D M-mode probing in the long axis, Doppler pulse wave analysis and by twelve-lead electrocardiography (Hodgson et al., 2004, Am. J. Physiol., 287:H471-H479), and invasively with intraventricular microcatheterization (Millar). For histopathology, harvested heart tissue was fixed for 1 h in 3% paraformaldehyde, paraffin sectioned, and subjected to antigen retrieval followed by confocal examination using CFP antibody for cell tracking (1:500, Molecular Probes) in combination with α-actinin for sarcomere visualization and DAPI nuclear stain. Transgenic cardiac-restricted overexpression of the cytokine TNFα was achieved using the α-myosin heavy chain promoter linked to the TNFα transgene (Sivasubramanian et al., 2001, Circulation, 104:826-831). Disrupting the kinase domain of the TGF-β receptor (ATGFβRII) or overexpression of the BMP inhibitor noggin was used to ablate the capacity of embryonic stem cells to respond to cardiogenic cues (Behfar et al., 2002, FASEB J., 16:1558-1566).

Statistical Analysis.

Comparison between groups was performed using a standard t-test of variables with 95% confidence intervals.

Example 6

Procuring Cardioprogenitors and their Use in Stem Cell Therapy

Figure 11:
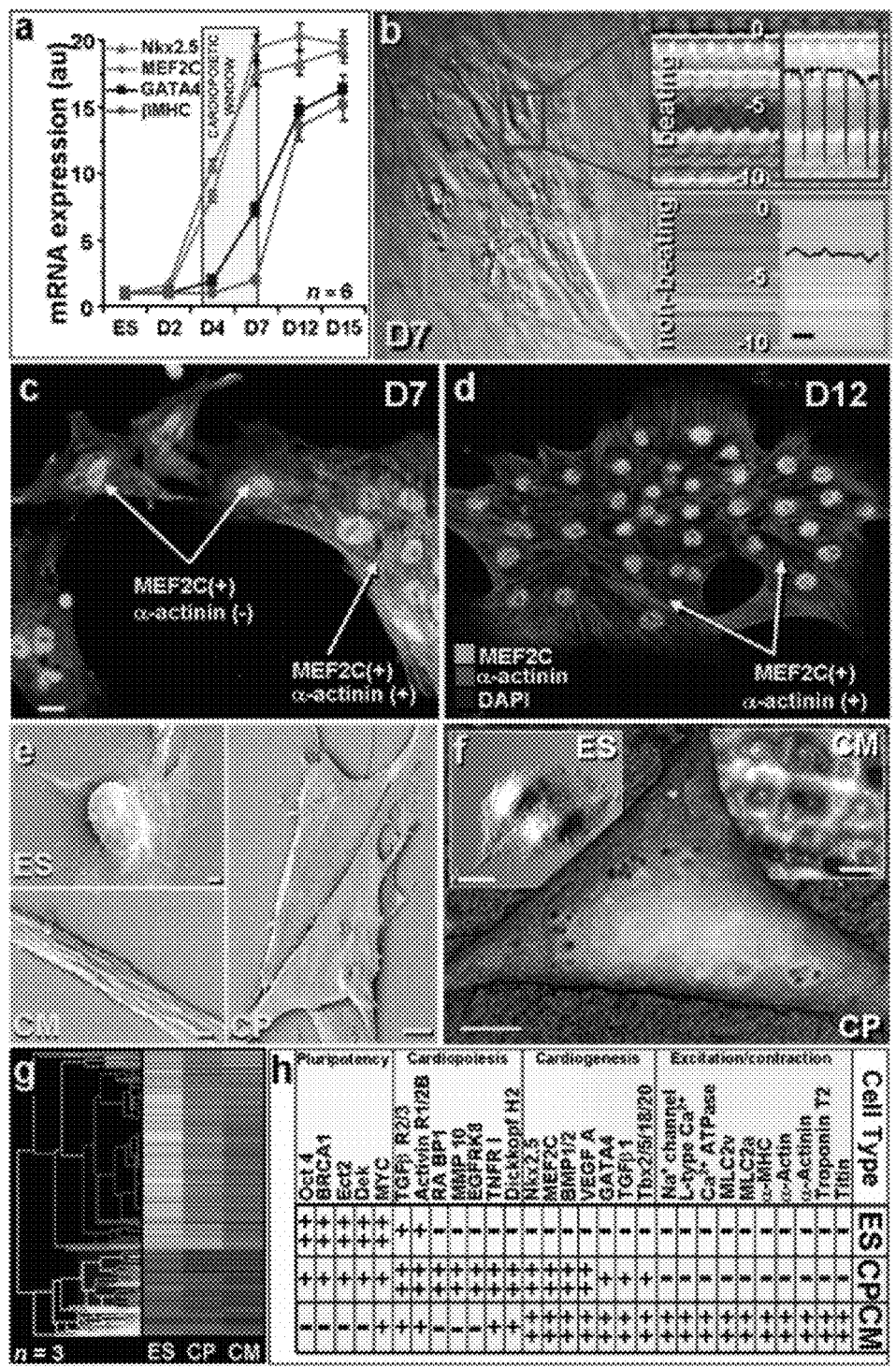
FIG. 11A is a graph showing that up-regulation of cardiac transcription factors Nkx2.5, MEF2C and GATA4 preceded sarcomeric βMHC gene expression on Q-RT-PCR.
FIG. 11B-D shows a non-beating cell population with nuclear (DAPI co-localized) translocation of cardiac transcription factors lacking sarcomeres (MEF2C(+), α-actinin(−)), isolated at day seven of differentiation (D7), formed syncitia of beating cardiomyocytes (MEF2C(+), α-actinin(+)) by D12. Inset in FIG. 11B shows the cell contractility by line scan.
FIG. 11E-F shows embryonic (ES), cardiopoietic (CP) and cardiomyocyte (CM) phenotypes resolved with field emission scanning electron microscopy (FIG. 11E) and atomic force microscopy (FIG. 11F).
FIG. 11G shows a gene array dendogram of ES, CP and CM.
FIG. 11H shows distinct expression profiles of markers for pluripotency (upregulated in ES), cardiopoiesis (upregulated in CP), cardiogenesis (upregulated in CP and CM) and excitation-contraction coupling (upregulated in CM). Minus: background expression; plus: definitive expression used as baseline; double plus: ≥2-fold increase in expression. Scale bars: 1 s (FIG. 11B inset); 5 μm (FIG. 11C, E, F for CP); 10 μm (FIG. 11F for ES); and 2 μm (FIG. 11F for CM).

Despite their proclivity for cardiogenesis, the hazard of neoplastic escape from cardiogenic signals has made therapy with embryonic stem (ES) cells controversial, necessitating discovery of a safe alternative (Chien et al., 2004, Science, 306:239-240; Menasche, 2004, Nat. Biotechnol., 22:1237-1238; Foley & Mercola, 2004, Trends Cardiovasc. Med., 14:121-125; Kehat et al., 2004, Nat. Biotechnol., 22:1282-1289; Behfar et al., 2002, FASEB J., 16:1558-1566). Within the continuum of embryonic stem cell differentiation, upregulation of cardiac transcription factors (e.g., Nkx2.5, MEF2C and GATA4) (Srivastava & Olson, 2000, *Nature*, 407:221-226) preceded sarcomeric gene expression (e.g., βMHC) distinguishing the process of cardiac pre-determination in the early embryoid body (FIG. 11A). Dissection of the embryoid body during this cardiopoietic window uncovered a precursor cell population that demonstrated nuclear import of transcription factors driving cardiac differentiation upon isolation from their embryonic stem cell-derived mesodermal origin (FIG. 11B-C). The captured cardiopoietic stem cells were en route to maturation, undergoing myofibrillogenesis to form contracting cardiomyocytes (CM; FIG. 11D). Ultrastructural dissection with nanoscale deconvolution underscored the transitional state of cardiopoietic stem cells during cardiogenic metamorphosis from a phenotype of high nucleus to cytosol ratio, typical of embryonic stem cells, towards acquisition of a striated cardiac structure (FIG. 11e-f). With a gene/protein profile distinct from the pluripotent source or cardiomyocyte progeny (see, for example, Table 1), the molecular fingerprint of cardiopoietic stem cells indicated definitive commitment to the cardiac program (FIG. 11G-H). Down-regulation of pluripotent markers (e.g., Oct4) (Nichols et al., 1998, *Cell*, 95:379-391) and oncogenes (e.g., BRCA1, MYC) (Shachaf et al., 2004, *Nature*, 431:1112-1117) along with activation of cardiogenic pathways, preceding the expression of the excitation-contraction machinery, secured the conversion from a tumourigenic undifferentiated stage to engagement into the cardiac-specific cell lineage (FIG. 11H).

TABLE 1

Markers present in embryonic stem cells, cardiopoietic stem cells, and cardiomyocytes.

| Gene/Protein Name | ESC Expression | CSC Expression | CM Expression |
|---|---|---|---|
| Oct4 | ++ | + | − |
| DEK | ++ | + | − |
| BRCA1 | ++ | + | − |
| Ect2 | ++ | + | − |
| MYC | ++ | + | − |
| Fosb | − | + | ++ |
| NRAP | − | + | ++ |
| MEF2A | − | + | ++ |
| Furin | − | + | ++ |
| TGFβ1 | − | + | ++ |
| fibronectin receptor α | − | + | ++ |
| discoidin domain receptor 1 | − | + | ++ |
| bag2 | − | + | ++ |
| cystein rich protein | − | + | ++ |
| CUGBP2 | − | + | ++ |
| NDRG4 | − | + | ++ |
| CBP/p300 inhibitory protein 1 | − | + | ++ |
| interferon inducible protein 1 | − | + | ++ |
| tropomyosin 1, alpha | − | + | ++ |
| Rho GTPase activating protein 1 | − | + | ++ |
| carboxypeptidase D | − | + | ++ |
| profilin 2 | − | + | ++ |
| transforming growth factor beta 1 induced transcript 1 | − | + | ++ |
| tropomyosin 1, alpha | − | + | ++ |
| growth hormone receptor | − | + | ++ |
| vinculin | − | + | ++ |
| adenylate cyclase 6 | − | + | ++ |
| S100 calcium binding protein A1 | − | + | ++ |
| tropomyosin 2, beta | − | + | ++ |
| retinol binding protein 1, cellular | − | + | ++ |
| Moesin | − | + | ++ |
| Annexin A6 | − | − | ++ |
| Connective Tissue Growth Factor | − | − | ++ |
| Smad6 | − | − | ++ |
| Na+ channel | − | − | ++ |
| L-Type Ca2+ channel | − | − | ++ |
| Ca2+ ATPase | − | − | ++ |
| MLC2V | − | − | ++ |
| MLC2a | − | − | ++ |
| α-MHC | − | − | ++ |
| α-actin | − | − | ++ |
| α-actinin | − | − | ++ |
| Troponin T2 | − | − | ++ |
| Titin | − | − | ++ |
| integral membrane protein 2A | − | ++ | − |
| insulin-like growth factor binding protein 4 | − | ++ | − |
| thymus cell antigen 1, theta | − | ++ | − |
| selenoprotein P, plasma, 1 | − | ++ | − |
| glycoprotein 38 | − | ++ | − |
| epidermal growth factor receptor pathway substrate 8 | − | ++ | − |
| heat shock protein 1A | − | ++ | − |
| cellular retinoic acid binding protein I | − | ++ | − |
| placenta-specific 8 | − | ++ | − |
| matrix metalloproteinase 2 | − | ++ | + |
| secreted acidic cysteine rich glycoprotein | − | ++ | + |
| mannosidase 1, alpha | − | ++ | + |
| lectin, galactose binding, soluble 1 | − | ++ | + |
| S100 calcium binding protein A6 (calcyclin) | − | ++ | + |
| epoxide hydrolase 1, microsomal | − | ++ | + |
| pleiomorphic adenoma gene-like 1 | − | ++ | + |
| insulin-like growth factor 2 | − | ++ | + |
| tubby like protein 4 | − | ++ | + |
| prion protein | − | ++ | + |
| FK506 binding protein 10 | − | ++ | ++ |
| cyclin D2 | − | ++ | ++ |
| reticulocalbin 3, EF-hand calcium binding domain | − | ++ | ++ |
| selenoprotein M | − | ++ | ++ |
| cyclin-dependent kinase inhibitor 1A (P21) | − | ++ | ++ |
| caldesmon 1 | − | ++ | ++ |
| integrin beta 1 (fibronectin receptor beta) | − | ++ | ++ |
| transcobalamin 2 | − | ++ | ++ |
| annexin A2 | − | ++ | ++ |
| cyclin-dependent kinase inhibitor 1A (P21) | − | ++ | ++ |
| thrombospondin 1 | − | ++ | ++ |
| monocyte to macrophage differentiation-associated | − | ++ | ++ |
| AXL receptor tyrosine kinase | − | ++ | ++ |
| annexin A5 | − | ++ | ++ |
| muscleblind-like 2 | − | ++ | ++ |
| annexin A1 | − | ++ | ++ |
| procollagen, type IV, alpha 1 | − | ++ | ++ |
| calpain 2 | − | ++ | ++ |
| epithelial membrane protein 1 | − | ++ | ++ |
| protease, serine, 11 | − | ++ | ++ |
| tropomyosin 2, beta | − | ++ | ++ |
| lectin, galactose binding, soluble 9 | − | ++ | ++ |
| annexin A3 | − | ++ | ++ |

Figure 12:
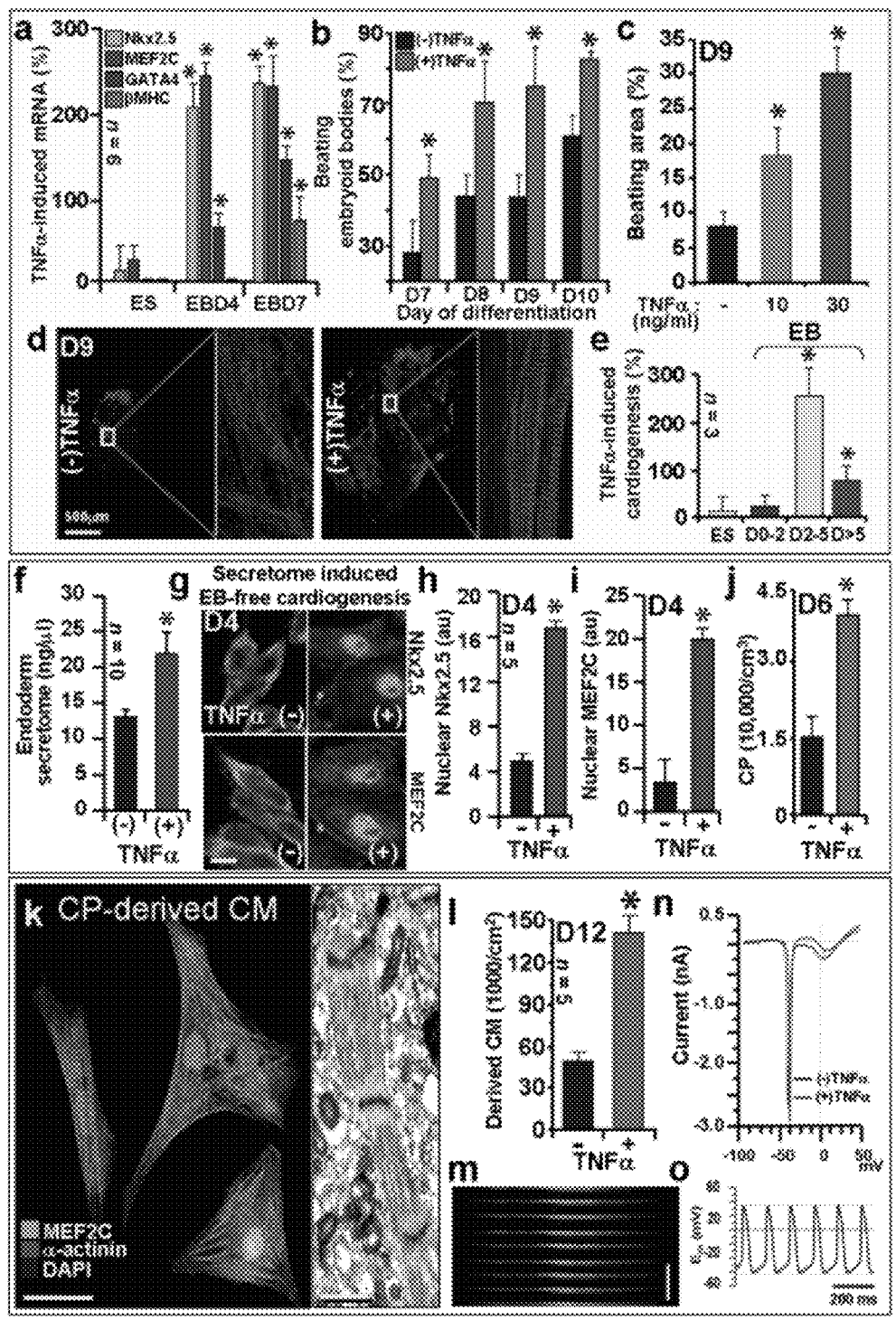
FIG. 12A-D demonstrate that in embryoid bodies (EB), TNFα amplified cardiac transcription factors, promoting cardiogenesis and augmenting cardiac content visualized by α-actinin immunofluorescence.
FIG. 12E-F show that the peak TNFα cardiogenic effect correlated with up-regulation of the endodermal secretome.
FIG. 12G-J demonstrates that guided cardiogenesis of embryonic stem cell monolayers was promoted by TNFα-primed endodermal conditioned medium, efficiently recruiting cardiopoietic stem cells (CP).
FIG. 12K shows that recruited cardiopoietic cells yielded cardiomyocytes (CP-derived CM) that recapitulated cardiac structure on confocal and transmission electron microscopy.
FIG. 12L-O shows that CP-derived CM demonstrated calcium transients, inward ion currents on voltage-clamp and action potential activity on current-clamp. Scale bars: 10 μm (FIG. 12G, K; confocal); 1 μm (FIG. 12K, electron); and 3 s (FIG. 12M).
Figure 13:
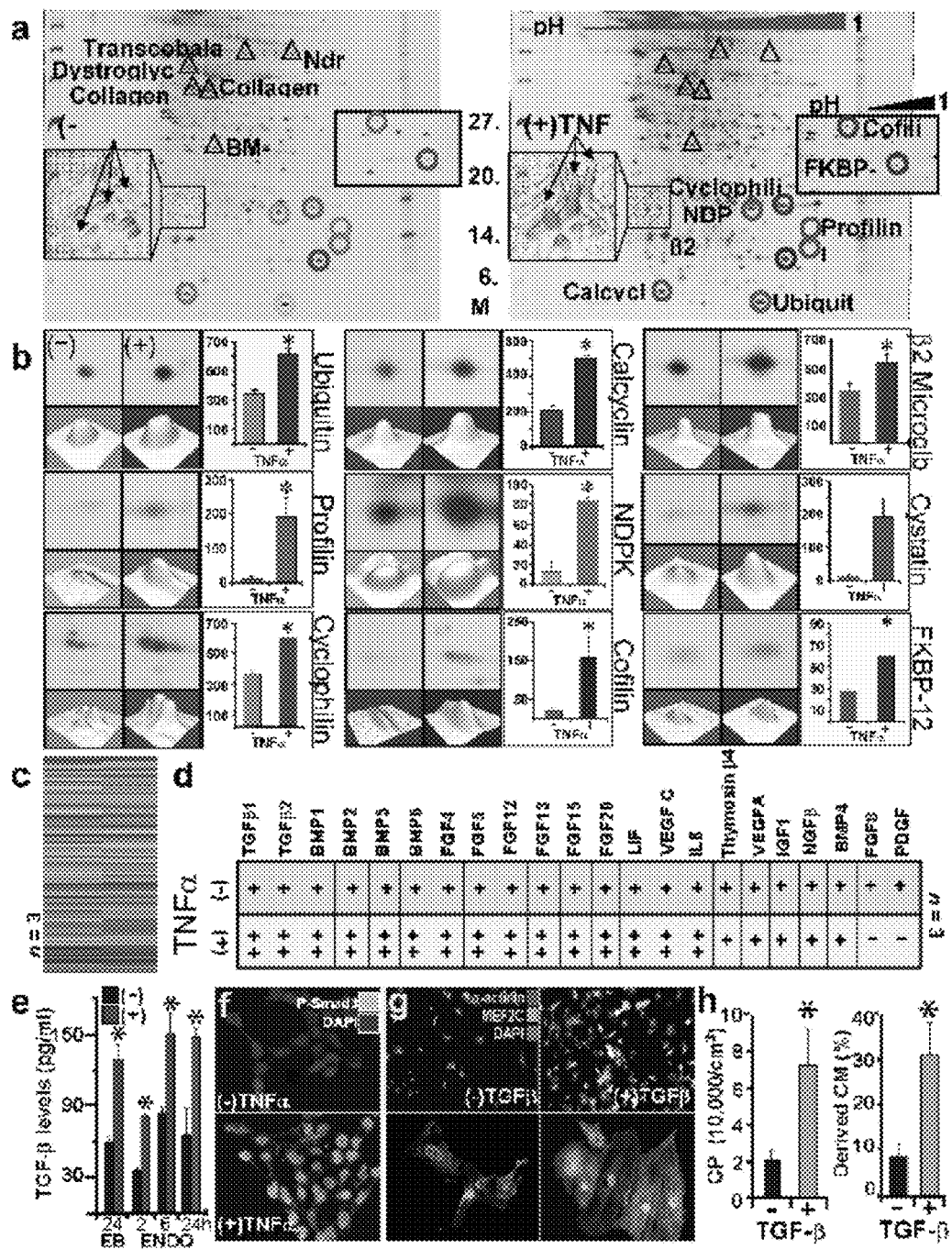
FIG. 13A shows 2-D gels of the secretome from naïve versus TNFα-primed endoderm at multiple pH gradients. Coloured circles: TNFα-upregulated proteins; black triangles: down-regulated or unchanged proteins. Inset: TNFα molecule in the cytokine-primed secretome.
FIG. 13B shows the cocktail of up-regulated secretome proteins identified by mass spectrometry (profilin/cofilin: involved in sarcomerogenesis; calcyclin: a calcium signalling protein; NDPK: associated with cardiac gene reprogramming; FKBP12/cystatin/ubiquitin: implicated in heart formation; and β2 microglobulin: a marker of TNFα stimulation); minus (unprimed secretome); plus (TNFα-primed secretome).
FIG. 13C demonstrates TNFα reprogramming of endoderm shown on a gene microarray.
FIG. 13D shows the endoderm-derived secretome growth factor expression pattern in response to TNFα-priming assessed by tandem genetic and proteomic probing.
FIGS. 13E and F show transforming growth factor-beta (TGF-β) up-regulation in TNFα-primed embryoid body (EB) or endodermal conditioned medium (ENDO) confirmed by immune assay, associated with augmented TGF-β-dependent Smad3 signalling in differentiating embryonic stem cells.
FIGS. 13G and H shows TGF-β addition, which emulates TNFα-priming, increased proliferation and cardiac differentiation of purified cardiopoietic stem cells.

In the embryo, cardiac transformation of the mesoderm requires endodermal signalling (Foley & Mercola, 2004, *Trends Cardiovasc. Med.*, 14:121-125; Srivastava & Olson, 2000, *Nature*, 407:221-226). Cardiopoiesis was fostered in embryoid bodies by the reprogramming cytokine tumour necrosis factor alpha (TNFα) (Locksley et al., 2001, *Cell*, 104:487-501), as demonstrated through the up-regulated expression of transcription factors, acceleration of cardiogenesis and increased cardiac content (FIG. 12A-D). Maximal between day 2 and day 5 of embryoid body differentiation (FIG. 12E), the TNFα effect on cardiogenesis manifested as a doubling of the protein concentration within the endodermal secretome (FIG. 12F). Application of the conditioned medium derived from the TNFα-primed endoderm guided vigorous differentiation of pluripotent embryonic stem cells directly into cardiopoietic stem cells, eliminating the need for transit through an embryoid body (FIG. 12G-J). Cardiopoietic stem cells derived extra-embryo maintained mitotic activity, clonal expansion and resilience to hypoxic stress (5% $O_2$), remnants of their embryonic source, yet acquired contact inhibition and could reproducibly generate sarcomeres to complete the cardiac program (FIG. 12K). In this way, recruited cardiopoietic stem cells provided a renewable source that yielded functional cardiomyocytes with calcium transients, ion currents and action potential activity, demonstrative of the cardiac phenotype with no evidence for dedifferentiation (FIG. 12L-O).

TNFα amplification of cardiopoiesis (FIG. 12F-J) was due to a re-distribution of the endodermal secreted protein content (FIG. 13A-D). In particular, a cocktail of over twenty proteins within the endodermal secretome were found up-regulated, ranging from factors involved in sarcomerogenesis (profilin, cofilin) (Obinata et al., 1997, Cell Struct. Funct., 22:181-189; Mohri et al., 2000, J. Muscle Res. Cell. Motil., 21:49-57), calcium signaling (calcyclin) (Edgeworth et al., 1989, Nature, 342:189-192), myocardial reprogramming (NDPK) (Lutz et al., 2004, Methods Enzymol., 390:403-418) and heart formation (FKBP12, cystatin, ubiquitin) (Xin et al., 2002, Nature, 416:334-338; Smart et al., 2002, Gene Expr. Patterns, 2:61-67; Kwon et al., 2002, Science, 297:96-99) to potent cardiogenic growth factors including TGF-β and FGF superfamily members (Behfar et al., 2002, FASEB J., 16:1558-1566; Mummery et al., 2003, Circulation, 107:2733-2740), catalogued by proteomic and/or genomic probing (FIG. 13A-D). Quantification of endoderm secreted proteins confirmed the generated profile of the TNFα-primed cocktail, exemplified by the enzyme-linked immunosorbent assay of TGF-β whose levels were further corroborated by activation of intracellular P-Smad3 signaling (Daniels et al., 2004, J. Clin. Invest., 114: 1308-1316) in stem cells undergoing cardiopoiesis (FIG. 13E-F). Supplementation of the endoderm-derived unprimed conditioned medium with TGF-β, titrated to match TNFα-induced up-regulation, stimulated purified cardiopoietic stem cells to proliferate and differentiate (FIG. 13G-H). Identification of components within the endodermal secretome thus facilitated manipulation of cardiopoiesis, streamlining the switch from pluripotency to cardiogenic transformation for macroscale production of cardiopoietic stem cells ex vivo.

Figure 14:
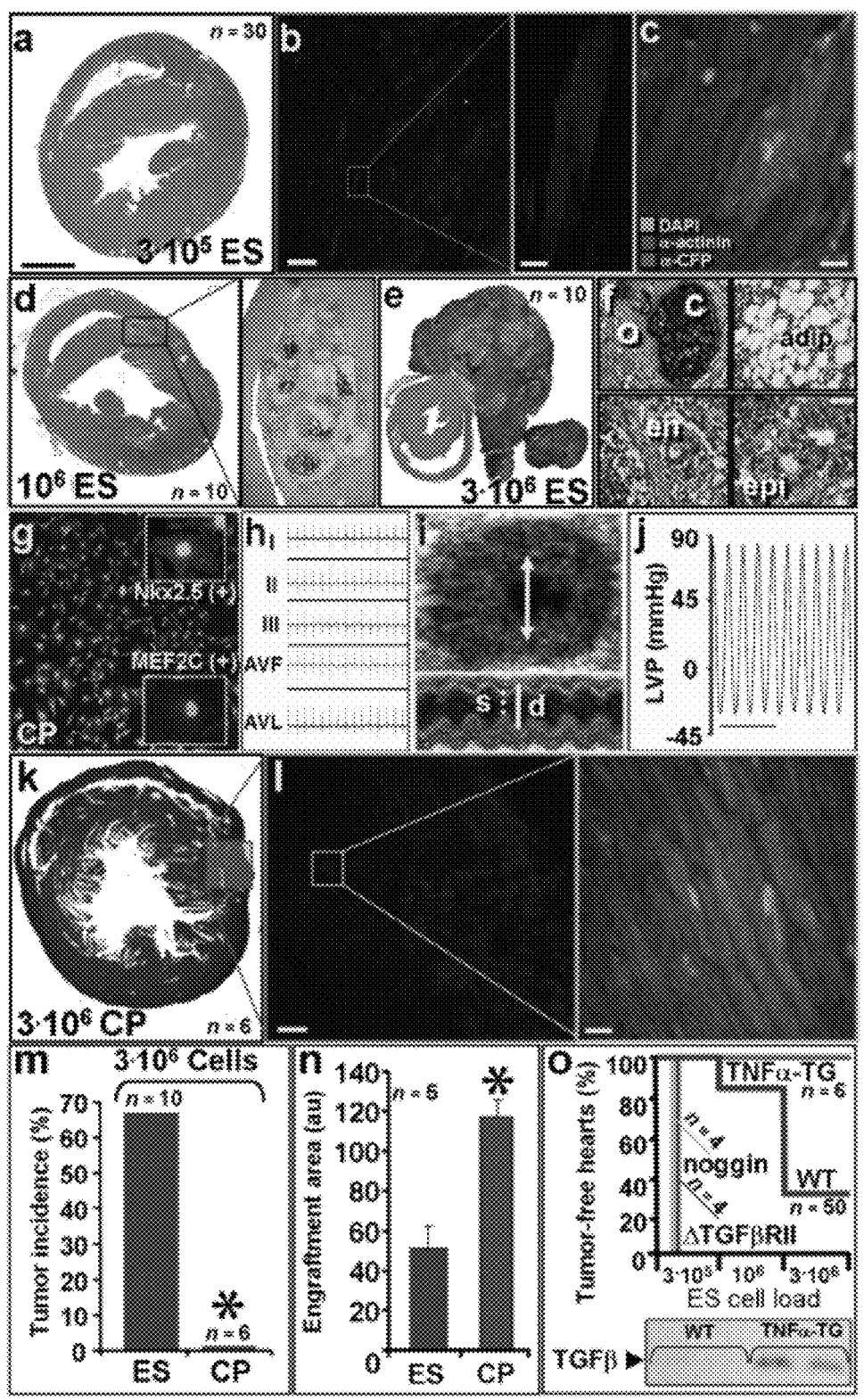
FIG. 14A-C shows that embryonic stem cells (ES≥3·10$^5$/heart) transplanted by echocardiography-guided cell delivery resulted in cyan fluorescent ES-derived cardiomyocytes embedded into actinin-positive host heart.
FIG. 14D-F shows that ES injected at ≥10$^6$/heart increased the risk for uncontrolled growth, generating teratoma consisting of osteoblasts (O), chondrocytes (C), adipocytes (adip), endothelial (en) or epithelial (epi) cell types.
FIG. 14G shows that ES-derived cardiopoietic stem cells (CP), positive for cardiac transcription factors, were recruited using TNFα-primed endodermal conditioned medium.
FIG. 14H-J demonstrate that delivery of CP at 3×10$^6$/heart resulted in synchronous cardiac rhythm and vigorous function monitored by multi-lead electrocardiography, ultrasound (two-headed arrow, plane of M-mode probing; s, systole; d, diastole) and micropressure ventricular catheterization (LVP, left ventricular pressure).
FIGS. 14K and L show that CP treatment resulted in proper implantation and cardiac differentiation within host heart.
FIGS. 14M and N show that in contrast to ES, delivery of 3×10$^6$ CP was not associated with tumour formation and led to enhanced engraftment.
FIG. 14O demonstrates that compared to naïve wild-type (WT) hearts, transgenic recapitulation of TNFα-priming, through cardiac-restricted overexpression (TNFα-TG), reduced the risk for tumourigenesis associated with ES transplantation by augmenting myocardial expression of TGF-β, determined by Western blot (inset). Disruption of cardiopoietic signalling in ES cells, through deletion of the kinase domain of the TGF-β receptor (ΔTGFβRII) or overexpression of the BMP inhibitor noggin, increased tumour risk. Scale bars: 2 mm (FIG. 14A); 70 μm (FIG. 14B, L); and 10 μm (FIG. 14B inset, FIG. 14C, 1 inset).

The therapeutic value of cardiopoietic stem cell use was assessed in vivo upon echocardiography-guided transplantation. Loads of ≤3×10$^5$ pluripotent cells per heart led to incorporation of embryonic stem cell-derived cardiomyocytes into recipient heart muscle (FIG. 14a-c), but increases in cell dose precipitated neoplastic invasion (FIG. 14D-F) demonstrating the low therapeutic index of embryonic stem cell-based treatment. In contrast, delivery of ≥3×·10$^6$ cardiopoietic stem cells, recruited in vitro from a monolayer of embryonic stem cells using the here identified cardiogenic cocktail (FIG. 14G), resulted in electricomechanical coupling in the recipient heart with robust contractile performance reflective of successful alignment of transplanted cells within the myocardium (FIG. 14H-J). Indeed, transplanted cardiopoietic stem cells reproducibly underwent cardiac differentiation and extensive engraftment within the host myocardium, with no evidence for tumour formation on histopathologic examination (FIG. 14K-M). In fact, cardiopoietic stem cell use surpassed the maximum therapeutic outcome achievable with embryonic stem cell delivery (FIG. 14N). Impeding cardiopoiesis through genetic ablation of the stem cell capacity to recognize cocktail components (e.g., TGFβ/BMP), exaggerated the risk for tumourigenesis (FIG. 14O). Conversely, cardiac-restricted transgenic TNFα overexpression (TNFα-TG) augmented the host heart cardiogenic capacity (FIG. 14O inset) and reduced the risk for carcinogenesis upon embryonic stem cell transplantation (FIG. 14O), demonstrating that mimicry of cardiopoiesis can be achieved in situ.

The promise of embryonic stem cells in this era of regenerative medicine has remained unfulfilled, limited by the propensity for carcinogenic transformation inherent to pluripotency. This impasse, preventing therapeutic application, was here solved by lineage-specific recruitment of an embryonic stem cell-derived intermediate to serve as a safe and efficacious alternative. The paradigm of honing cellular plasticity to nullify malignant risk thus provides a means by which to bypass the shortcomings of embryonic stem cell therapy.

Example 7

Components of a Cardiogenic Cocktail

Based on the above-described experiments, the following components were determined to be endoderm derived: caspase-4; chemokine ligand 1; chemokine ligand 2; chemokine ligand 5; chemokine ligand 7; chemokine ligand 11; chemokine ligand 20; haptoglobin; colony stimulating factor 1; lectin; cholesterol 25-hydroxylase; syntaxin 8; syntaxin 11; ceruloplasmin; complement component 1; complement component 3; platelet derived growth factor; integrin alpha 6; lysosomal acid lipase 1; leukemia inhibitory factor; insulin growth factor-1; interleukin 6; beta-2 microglobulin**; ubiquitin; macrophage migration inhibitory factor; retinoic acid; TGF-β1; TGF-β2; BMP1; BMP2; BMP4; BMP5; BMP6; FGF4; FGF5; FGF12; FGF13; FGF15; FGF20; VEGF C; cofilin; cyclophillin A; FKBP12; NDPK; profilin 1; cystatin C; calcyclin; and ubiquitin.

A cardiogenic cocktail was generated containing the indicated amount of each component: TGF-β1 (2.5 ng/ml); TGF-β2 (2.5 ng/ml); BMP-1 (5 ng/ml); BMP-2 (5 ng/ml); BMP-5 (5 ng/ml); BMP-6 (5 ng/ml); FGF-4 (10 ng/ml); FGF-5 (10 ng/ml); FGF-12 (10 ng/ml); FGF-13 (10 ng/ml); FGF-15 (10 ng/ml); FGF-20 (10 ng/ml); leukemia inhibitory factor (1000 U/ml); VEGF-C (15 ng/ml); and interleukin 6 (100 ng/ml).

The following components were exogenously added to the above-described endoderm-derived. IGF-1 (50 ng/ml); IL-6 (100 ng/ml); FGF-4 (10 ng/ml); TGFβ (25 ng/ml); BMP (5 ng/ml); LIF (100 U/ml); and hα-thrombin (40 nM).

In summary, the cardiogenic cocktail described herein contains 54 components; 47 components that are endoderm derived and 7 components that are exogenously added.

Example 8

Additional Materials and Methods

Embryonic stem cell culture and embryoid body differentiation. The pluripotent murine embryonic stem cell lines (i.e., CGR8, D3, 129 and R29) were propagated in GMEM medium with pyruvate, non-essential amino acids, mercaptoethanol, 7.5% fetal calf serum (FCS) and leukemia inhibitory factor (LIF, ESGRO), as described (Terzic et al., 2003, Circ Res., 92:444-452; Behfar et al., 2002, FASEB J., 16:1558-1566). Cells were split every two days to maintain undifferentiated status or differentiated using the "hanging drop" method (Terzic et al., 2003, *Circ Res.*, 92:444-452; Behfar et al., 2002, *FASEB J.*, 16:1558-1566). Drops of differentiation medium (GMEM with selenium, pyruvate, non-essential amino acids, mercaptoethanol, 20% FCS, without LIF), containing 500 embryonic stem cells, were placed for two days on a plate-lid to allow embryoid body organization. Embryoid bodies, suspended for three days, were plated on gelatin-coated dishes for seven days. Formation of contracting areas in the mesoderm was monitored with microscopy, with cardiac content assessed using the monoclonal cardiac sarcomeric α-actinin antibody (Behfar et al., 2002, *FASEB J.*, 16:1558-1566).

Embryoid Dissociation and Characterization.

Embryoid bodies, at different stages of differentiation, were detached from dishes with 0.05% trypsin, and dissociated using 1 mg/ml collagenase (CLSII, Worthington) and 0.25 mg/ml pancreatin in (in mmol/L) NaCl-117, HEPES 20, $NaH_2PO_4$ 1.2, KC15.4, $MgSO_4$ 1 and glucose 5 (pH 7.35) (Terzic et al., 2003, *Circ Res.*, 92:444-452). Embryoid body cell suspensions were characterized for progenitor content by confocal immunofluorescent probing in addition to video microscopy. Purification of cardiopoietic stem cells and cardiomyocytes was accomplished through use of a discontinuous 2-layer percoll density gradient based on their mass-to-volume properties (cardiomyocytes—D=1.07/1.09; cardiopoietic—D=1.07/1.09 first, then D=1.05/1.09). The same approach can be applied to purify cardiopoietic stem cells and cardiomyocytes following guided differentiation of embryonic stem cells monolayers. To monitor cell division, purified cells were cultured in a temperature- and gas-controlled chamber (37° C., 5% $CO_2$), set on a stage of a CCD camera-coupled microscope, with phase contrast images acquired serially.

Immunocytochemistry and Immunofluorescence.

Embryonic stem cells, cardiopoietic stem cells and derived cardiomyocytes, grown on coverslips, were rinsed with phosphate buffered saline (PBS), fixed in 3% paraformaldehyde (PFA) and permeabilized with 0.1% TritonX-100. To prevent non-specific staining, coverslips were incubated with a blocking buffer (Superblock™, Pierce Biotech) following fixation. Blocking buffer was removed, and antibodies were added (Nkx2.5 1:400; MEF2C 1:500; GATA4 1:300; α-Actinin 1:1000; L-type $Ca^{2+}$ channel 1:400; Cx43 1:500; Kir6.2 1:500; GFP 1:400) overnight at 4° C. The following day, primary antibodies were rinsed-off using wash buffer, and ALEXA-conjugated secondary antibodies (1:500) was applied. Secondary antibody was rinsed off using wash buffer, and the DNA-stain DAPI was incubated prior to mounting. Fluorescent excitation of stained cellular components were accomplished by concurrent use of the UV (350-370 nm), Arg/Kry (488 nm), and HeNe (568, 633 nm) laser lines for multi-color Meta-based confocal microscopy (Zeiss). Acquired images were analyzed using Axioplan software (Zeiss). Additionally, cardiopoietic stem cell proliferation and purity was assessed by ArrayScan high-throughput multichannel fluorescence automated microscopy (Cellomics) using MEF2C and α-actinin antibodies, along with DAPI staining.

RNA Isolation and Genomic Profiling.

Total RNA was isolated from embryoid bodies, as well as from embryonic stem cells and when derived from cardiopoietic stem cells and cardiac cell progeny using the Micro-to-Midi isolation kit (Invitrogen). Total RNA was also be attained from TNFα-primed and unprimed endodermal cells. RNA samples was analyzed using Affymetrix microarrays where comparative gene expression profiles of embryoid bodies, as well as embryonic versus cardiopoietic stem cells or cardiomyocytes, and in separate studies unprimed versus TNFα-primed endoderm was attained by labelled cRNA hybridization to the mouse genome 430 2.0 array using standard protocols (Affymetrix). Data was acquired with a Gene-Chip Scanner 3000 (Affymetrix), and analyzed with the GeneSpring software (Silicon Genetics). Data population sets were normalized to the undifferentiated or unprimed phenotype, and quality filtered to eliminate background noise prior to hierarchical clustering. Data was confirmed by subjecting sample total RNA to real time Q-RT-PCR, using primers specifying each gene identity (Behfar et al., 2002, *FASEB J.*, 16:1558-1566).

Two-dimensional gel electrophoresis. To resolve the proteomic phenotype of cardiopoietic stem cells versus their source and progeny, cellular proteins was solubilized in isoelectric focusing (IEF) buffer (7 M urea, 2 M thiourea, 2% CHAPS, with protein concentrations determined by protein assay. Two-dimensional gel electrophoresis (2-DE) was carried out in the first dimension (IEF) using a Protean® IEF cell (Bio-Rad). Protein samples will be added to 300 μl of IEF buffer, supplemented with DTT (dithiothreitol) and ampholytes (Bio-Rad), and then taken up by active rehydration into immobilized pH gradient (IPG) Ready Strips™ (170 mm linear gradient strips, pH 3-10 or 4-7, Bio-Rad) at 50 volts (V) for 10 h. IEF then followed, using a series of rapid ramping voltage steps for 15 min each at 100, 500, and 1000 V, followed by 10000 V for 60 kiloV-h. A variation of this process using passive rehydration was used for IEF of basic proteins (pH 6-11). Prior to second dimension sodium dodecyl sulfate-polyacrylamide gel electrophoresis (SDS-PAGE), focused IPG strips were equilibrated in a two-step process to ensure protein solubility, first by incubation in equilibration buffer (50 mM Tris-HCl, pH 8.8, 6 M urea, 30% v/v glycerol, 2% w/v SDS) supplemented with 10 mg/ml DTT, followed by incubation in equilibration buffer supplemented with 25 mg/ml iodoacetamide. Strips were then rinsed with SDS-PAGE buffer (25 mM Tris, 192 mM glycine, pH 8.3, 0.1% w/v SDS), and the proteins resolved by 12.5% SDS-PAGE using a Protean® II Xi system (Bio-Rad). Following SDS-PAGE, 2-D gels were silver-stained for compatibility with subsequent analysis of protein by mass spectrometry (Shevchenko et al., 1996, *Anal. Chem.*, 68:850-858). Using PDQuest 2-D gel analysis software (Bio-Rad), silver-stained gels were scanned, with protein spots detected, quantified, matched to spots on other gels, normalized, and statistically analyzed to determine the presence and extent of changes in the protein expression profiles at different stages of cardiac differentiation. Protein spots of interest were isolated and destained (Gharandaghi et al., 1999, *Electrophoresis*, 20:601-605) to ensure removal of silver, then digested with trypsin, extracted, dried under vacuum, and stored at −20° C. until mass spectrometric analysis.

Tandem Mass Spectrometry.

Tryptic peptides isolated from individual 2-D gel spots was reconstituted and resolved by high performance liquid chromatography (HPLC) on a C18 reversed phase (RP) column. Peptides were eluted from the RP-HPLC column with an increasing acetonitrile gradient, and electrosprayed into a Finnigan LCQ Deca ion trap mass spectrometer (Thermo Finnigan). Spectra of eluting peptides were acquired in a data-dependent fashion by first acquiring a full MS scan from m/z (mass/charge ratio) 150 to 2000 followed by MS/MS scans up to m/z 2000 to determine amino acid sequence following collision-induced dissociation of peptides that provide the most intense ions of the previous full MS scan. MS/MS spectra were searched against the SwissProt or NCBI non-redundant databases using both the SEQUEST and Mascot search algorithms to search both the 2+ and 3+ charge states of fragmented peptides. Results from each algorithm was cross referenced, providing more robust analysis than would either algorithm alone (Sadygov et al., 2004, *Nature Meth.*, 1:195-202).

Western Blotting.

Individual protein expression was probed after cellular harvest using 100 µl of RIPA buffer (50 mM Tris, 150 mM NaCl, 1 mM EDTA, 1 mM EGTA, 1% Triton X-10, 0.5% sodium deoxycholate, 0.1% SDS, pH 8.0) containing protease inhibitors. Samples were assayed for protein concentration and a working stock solution containing 4 mg/ml was created by diluting the sample in 2× Laemmli buffer. Samples were heated at 95° C. and 40-60 µg of total protein was loaded onto a 10% SDS-PAGE gel and electrophoresed. Proteins were transferred onto nitrocellulose membranes using either semi-dry or wet transfer conditions. Following transfer, membranes were incubated with 10 ml of blocking buffer (1×TBS, 0.1% Tween-20, 5% (w/v) skim milk powder, pH 7.5) at room temperature and then incubated with a primary antibody (1:1,000) diluted in primary solution (1×TBS, 0.1% Tween-20, 1% (w/v) skim milk powder, pH 7.5). Secondary antibody (1:10,000) made up in primary solution was added the following day after rinsing the primary off with wash buffer (1×TBS, 0.1% Tween-20, pH 7.5). Western blots were developed using the Pierce chemiluminescence kit and visualized using a UVP Bioimager.

Patch-Clamp.

Membrane electrical activity was determined by patch-clamp recording in the whole cell configuration using the current- or voltage-clamp mode (Axopatch 1C, Axon Instruments). Action potential profiles and voltage-current relationship was acquired and analyzed with the Bioquest software from cells, at different stages of cardiac differentiation and maturation, superfused with Tyrode solution (in mM: NaCl 137, KCl 5.4, $CaCl_2$ 2, $MgCl_2$ 1, HEPES10, glucose 10; pH 7.4 with NaOH) using patch pipettes (5-10 MΩ) containing (in mM) KCl 140, $MgCl_2$ 1, HEPES10, EGTA 5, and supplemented with 5 mM ATP (pH 7.2 adjusted with KOH). Electrophysiological measurements were performed at 31±1° C. using a temperature controller (HCC-100A, Dagan Corp.) equipped with a Peltier thermocouple (1,10).

Calcium Imaging.

Two-dimensional confocal images (Zeiss LSM 510 Axiovert) of stem cells undergoing cardiac transformation and maturation, and loaded with the $Ca^{2+}$-fluorescent probe Fluo3-AM (Molecular Probes), was acquired by laser confocal microscopy with the 488-nm line of an argon/krypton laser. Images were deconvoluted and analyzed using Metamorph software (Visitron Universal Imaging) (Terzic et al., 2003, *Circ Res.*, 92:444-452; Hodgson et al., 2004, *Am. J. Physiol.*, 287:H471-H479).

Transmitted/Field-Emission Scanning Electron and Atomic Force Microscopy.

Cells at different stages of cardiac differentiation were fixed in PBS with 1% glutaraldehyde and 4% formaldehyde (pH 7.2). For transmitted electron microscopy (TEM), cells were processed in phosphate-buffered 1% $OsO_4$, stained with 2% uranyl acetate, dehydrated in ethanol and propylene oxide, and embedded in epoxy resin. Thin (90-nm) sections were placed on copper grids, stained with lead citrate, and micrographs were taken with a JEOL electron microscope (Behfar et al., 2002, *FASEB J.*, 16:1558-1566). For field-emission scanning electron (FESEM) microscopy, plasma membrane was stripped using a hypotonic solution and 1% Triton X-100. Membrane-stripped cells or whole embryoid bodies were fixed with 1% glutaraldehyde and 4% formaldehyde in PBS. Specimens were rinsed in PBS with 1% osmium, dehydrated with ethanol and dried in a critical point dryer (Ted Pella). On coating with platinum, samples were examined on a Hitachi scanning microscope. Contact-mode atomic force microscopy (AFM) was performed with silicon nitride NP-S tips (spring constant: 0.58 N/m) using a Nanoscope III controller (Digital Instruments) (Behfar et al., 2002, *FASEB J.*, 16:1558-1566). Plasma membrane-stripped cells were fixed in situ and rinsed with nanopure water and air-dried. An E-type scanner, with linear scanning frequencies (5-15 Hz), will be used to build 512×512 pixel AFM images. Data was analyzed with the Nanoscope IIIa software, and three-dimensional images generated from topographical height information.

Cell Tracking In Vivo.

Embryonic stem cell clones were engineered to express either the green fluorescent protein (GFP), the enhanced cyan fluorescent protein (ECFP) or the cytosolic (or nuclear) lacZ under the control of the cardiac-specific α-actin or α-myosin promoter subcloned upstream of the reporter gene (Clontech). For tracking cell fate, reporter genes were subcloned downstream of 5'LTR promoter of the modified murine stem cell virus (MSCV) or the murine phosphoglycerate kinase (PGK) promoter, for stable and robust post-transplantational expression. Constructs were linearized, and introduced into embryonic stem cells by lipofectamine (Invitrogen) transfection (Terzic et al., 2003, *Circ Res.*, 92:444-452; Behfar et al., 2002, *FASEB J.*, 16:1558-1566). Alternatively, the reporter gene was packaged into an MMLV retroviral system for high-yield embryonic stem cell incorporation.

Myocardial Infarction Model.

Infarction was generated by ligation of the left coronary artery (LCA) following endotracheal intubation, ventilation and thoracotomy in C57BL/6 mice. Coronary occlusion was confirmed by acute inspection of color change of the left ventricle wall, and ST elevation on the electrocardiogram before chest closure. Sham-operated mice underwent the same surgical procedure without LCA ligation. Our experience reveals a <10% surgery-related mortality. Infarcted mice will receive various stem cell regimens, and followed from 1 to 12 months. In a separate set of experiments, mice deficient in $K_{ATP}$ channels, generated by targeted disruption of the Kir6.2 gene and backcrossed for five generations to a C57BL/6 background, will be compared to age- and sex-matched control mice (Seino & Miki, 2003, *Prog. Biophys. Mol. Biol.*, 81:133-176). All mice receive standard chow, with a 12-hour day/night cycle and observed daily until termination of studies.

Cardiac Function.

Left ventricular ejection fraction and fractional shortening was quantified by echocardiography in the awake animal (Acuson c256) (Kane et al., 2004, *Diabetes*, 53:S169-175). Left ventricular pressure recordings in vivo will be measured invasively by a 1.4-F micropressure catheter (SPR-671, Millar Instruments) following carotid arterial cannulation and advancement across the aortic valve.

Cardiac Remodeling.

Left ventricular chamber dimensions and wall thickness was quantified in vivo by trans-thoracic echocardiography in awake mouse with a 15-MHz linear transducer (Acuson c256) (Kane et al., 2004, *Diabetes*, 53:S169-175). Total heart weight, and left ventricle including septum (LV) was weighed ex vivo and normalized to body weight. The LV was then be either: i) fixed in 10% formalin, paraffin-embedded, and stained with hematoxylin/eosin and Masson's trichrome for light microscopy. Myocyte cross-sectional area, interstitial and perivascular fibrosis was quantified using MetaMorph software; ii) myocyte ultrastructure was examined by transmitted/scanning electron microscopy; iii) myocytes were stained for terminal deoxynucletidyl transferase-mediated dUTP nick end-labeling (TUNEL) and caspase-3, and undergo a DNA laddering assay to assess for apoptosis; iv) myocardial collagen content was measured by hydroxyproline assay.

Electrocardiography.

Electrocardiograms were recorded telemetrically in conscious, untethered mice from surgically implanted transmitters (Data Sciences International) (Terzic et al., 2003, *Circ Res.*, 92:444-452; 10). In addition 12-lead surface electrocardiograms were recorded in lightly isoflurane-anesthetized mice.

Statistical Analysis.

Comparison of parameters among normally distributed groups was performed using Student's t test or analysis of variance. Kruskal-Wallis test was used to compare non-parametric data. The Duncan's multiple range procedure was used to adjust multiple comparisons. Kaplan-Meier analysis with log-rank testing was employed for survival analysis. A difference at $p<0.05$ will be considered significant.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of making stem cells which have the ability to differentiate into cardiovascular tissue, comprising:
   (a) contacting a culture of pluripotent stem cells with a composition under conditions wherein said stem cells which have the ability to differentiate into cardiovascular tissue are formed in said culture, said composition comprising TGFβ1; BMP-2; FGF-4; leukemia inhibitory factor; insulin-like growth factor-1; and interleukin 6, and
   (b) identifying said stem cells which have the ability to differentiate into cardiovascular tissue from said pluripotent stem cells and from cardiomyocytes, if present, by:
      (i) an observed expression of at least one polypeptide selected from the group consisting of Oct4; DEK; BRCA1; Ect2; and MYC, and at least one of:
      (ii)(a) an observed increase in expression of one or more of Nkx2.5, MEF2C, and GATA4 as compared to a reference expression level of Nkx2.5, MEF2C, or GATA4; and
      (ii)(b) nuclear translocation of one or more of Nkx2.5, MEF2C, and GATA4 to the nuclei of the cell.

2. The method of claim 1, further comprising separating said stem cells which have the ability to differentiate into cardiovascular tissue from said pluripotent stem cells and from cardiomyocytes, if present.

3. The method of claim 1, wherein said composition further comprises TGFβ2; BMP-1; BMP-5; BMP-6; FGF-5; FGF-12; FGF-13; FGF-15; FGF-20; VEGF-C; caspase-4; chemokine ligand 1; chemokine ligand 2; chemokine ligand 5; chemokine ligand 7; chemokine ligand 11; chemokine ligand 20; haptoglobin; colony stimulating factor-1; lectin; cholesterol 25-hydroxylase; syntaxin-8; syntaxin-11; ceruloplasmin; complement component 1; complement component 3; platelet derived growth factor; integrin alpha 6; lysosomal acid lipase 1; β-2 microglobulin; ubiquitin; macrophage migration inhibitory factor; retinoic acid; cofilin; cyclophillin A; FKBP12; NDPK; profilin 1; cystatin C; calcyclin, hα-thrombin, or any combination thereof.

4. The method of claim 1, wherein said stem cells which have the ability to differentiate into cardiovascular tissue express:
   (a) at least one polypeptide selected from the group consisting of Oct4; DEK; BRCA1; Ect2; and MYC;
   (b) at least one polypeptide selected from the group consisting of Fosb; NRAP; MEF2A; Furin; and TGFβ1; and
   (c) at least one polypeptide selected from the group consisting of integral membrane protein 2A; insulin-like growth factor binding protein 4; thymus cell antigen 1, theta; selenoprotein P, plasma, 1; and glycoprotein 38.

5. The method of claim 1, wherein said stem cells which have the ability to differentiate into a cardiovascular tissue express:
   (a) at least one polypeptide selected from the group consisting of Oct4; DEK; BRCA1; Ect2; and MYC; and
   (b) at least one polypeptide selected from the group consisting of Fosb; NRAP; MEF2A; Furin; and TGFβ1.

6. The method of claim 1, wherein said stem cells which have the ability to differentiate into cardiovascular tissue express:
   (a) at least one polypeptide selected from the group consisting of Fosb; NRAP; MEF2A; Furin; and TGFβ1; and
   (b) at least one polypeptide selected from the group consisting of integral membrane protein 2A; insulin-like growth factor binding protein 4; thymus cell antigen 1, theta; selenoprotein P, plasma, 1; and glycoprotein 38.

7. The method of claim 1, wherein said stem cells which have the ability to differentiate into cardiovascular tissue express at least one polypeptide selected from the group consisting of integral membrane protein 2A; insulin-like growth factor binding protein 4; thymus cell antigen 1, theta; selenoprotein P, plasma, 1; and glycoprotein 38.

8. The method of claim 1, wherein said pluripotent stem cells express at least one polypeptide selected from the group consisting of Oct4; DEK; BRCA1; Ect2; and MYC.

9. A culture of stem cells which have the ability to differentiate into cardiovascular tissue obtained according to the method of claim 1.

* * * * *

UNITED STATES PATENT AND TRADEMARK OFFICE
CERTIFICATE OF CORRECTION

PATENT NO.        : 8,962,320 B2
APPLICATION NO.   : 13/433095
DATED             : February 24, 2015
INVENTOR(S)       : Andre Terzic and Atta Behfar It is certified that error appears in the above-identified patent and that said Letters Patent is hereby corrected as shown below:

In the claims
Column 32, line 35 (Claim 3), please delete "cyclophillin" and insert -- cyclophilin --, therefor.

Signed and Sealed this
Twenty-first Day of July, 2015

Michelle K. Lee
*Director of the United States Patent and Trademark Office*